(12) United States Patent
Kaplan et al.

(10) Patent No.: US 6,260,699 B1
(45) Date of Patent: *Jul. 17, 2001

(54) PACKAGED SYNTHETIC ABSORBABLE SURGICAL ELEMENTS

(75) Inventors: Donald S. Kaplan, Weston; Matthew E. Hermes, Easton; Ross R. Muth, Brookfield; David L. Brown, Wallingford; Henry A. Holzwarth, Weston, all of CT (US)

(73) Assignee: United States Surgical Corporation, Norwalk, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/474,340

(22) Filed: Jun. 7, 1995

Related U.S. Application Data

(63) Continuation of application No. 08/262,203, filed on Jun. 20, 1994, now Pat. No. 5,462,162, which is a continuation of application No. 07/911,981, filed on Jul. 10, 1992, now Pat. No. 5,366,081, which is a continuation of application No. 07/568,089, filed on Aug. 16, 1990, now Pat. No. 5,222,978, and a continuation-in-part of application No. 07/491,215, filed on Mar. 9, 1990, now Pat. No. 5,019,093, and a continuation-in-part of application No. 07/395,476, filed on Aug. 18, 1989, now abandoned, and a continuation-in-part of application No. 07/388,152, filed on Aug. 1, 1989, now abandoned, which is a continuation of application No. 07/344,745, filed on Apr. 28, 1989, now abandoned, and a continuation-in-part of application No. 07/227,699, filed on Aug. 3, 1988, now abandoned, and a continuation-in-part of application No. 07/221,308, filed on Jul. 19, 1988, now Pat. No. 5,051,272, which is a continuation-in-part of application No. 07/089,735, filed on Aug. 26, 1987, now abandoned, and a continuation-in-part of application No. 07/089,732, filed on Aug. 26, 1987, now abandoned.

(51) Int. Cl.$^7$ ................................................ A61B 17/06
(52) U.S. Cl. ....................... 206/339; 206/380; 206/63.3
(58) Field of Search ............................... 206/63.3, 339, 206/382, 438, 380, 383

(56) References Cited

U.S. PATENT DOCUMENTS

| | | | |
|---|---|---|---|
| 2,949,181 | * | 8/1960 | Buccino ............................. 206/63.3 |
| 3,338,019 | * | 8/1967 | Trewella et al. .................... 206/63.3 |
| 3,338,401 | * | 8/1967 | Regan, Jr. ........................... 206/63.3 |
| 3,376,973 | * | 4/1968 | Granowitz et al. ................. 206/63.3 |
| 3,728,839 | * | 4/1973 | Glick .............................. 206/63.3 X |
| 3,815,315 | * | 6/1974 | Glick .............................. 206/63.3 X |
| 3,939,969 | * | 2/1976 | Miller et al. ....................... 206/63.3 |
| 3,972,418 | * | 8/1976 | Schules et al. ..................... 206/63.3 |
| 4,699,271 | * | 10/1987 | Lincoln et al. .................... 206/63.3 |

* cited by examiner

Primary Examiner—Paul T. Sewell

(57) ABSTRACT

Synthetic absorbable sutures are filled with a stabilizing agent, preferably a mixture of glycerol and calcium lactate, and inserted into a retainer having a narrow convoluted passageway. The retainer is inserted into an open foil pouch with a package stabilizing element such as a paper sheet filled with stabilizing agent. The package containing the suture, retainer and package stabilizing element is sterilized, aerated, equilibrated to a relatively high moisture level, and sealed. Long lengths of suture and doubled-over and tripled-over suture may be withdrawn from the retainer with low force without damaging the suture. Bends and kinks in the suture are prevented so as to provide a synthetic absorbable suture having highly desirable out of package hand and feel. The suture an removed from the package exhibits improved tissue drag characteristics.

20 Claims, 9 Drawing Sheets

PACKAGED SYNTHETIC ABSORBABLE SURGICAL ELEMENTS

RELATED CASES

This case is filed as a continuation of U.S. Ser. No. 08,262,203 filed Jun. 20, 1994, now U.S. Pat. No. 5,462,162 which is a continuation of U.S. application Ser. No. 07/911,981 filed Jul. 10, 1992, now U.S. Pat. No. 5,366,081, which is a continuation of U.S. application Ser. No. 07/568,089 filed Aug. 16, 1990, now U.S. Pat. No. 5,222,978, continuation-in-part of U.S. patent application Ser. No. 07-089,735 filed Aug. 26, 1987and now abandoned; as a continuation-in-part of U.S. patent application Ser. No. 07-221,308 filed Jul. 19, 1988, now U.S. Pat. No. 5,501,272; as a continuation-in-part of U.S. patent application Ser. No. 07-388,152 filed Aug. 1, 1989, and now abandoned; as a continuation-in-part of U.S. patent application Ser. No. 07-395,476 filed Aug. 18, 1989 and now abandoned; and as a continuation-in-part of U.S. patent application Ser. No. 07-491,215 filed Mar. 9, 1990, now U.S. Pat. No. 5,019,193, which is a continuation of U.S. patent application Ser. No. 07-344,745 filed Apr. 28, 1989 and now abandoned, a continuation-in-part of U.S. patent application Ser. No. 07-227,699 filed Aug. 3, 1988 and now abandoned, a continuation-in-part of U.S. patent application Ser. No. 07-089,732 filed Aug. 26, 1987 and now abandoned.

TECHNICAL FIELD

The present invention relates to packaging of synthetic absorbable surgical elements and, more particularly to an improved package and method of providing packaged synthetic absorbable sutures having improved out of package handling characteristics.

BACKGROUND OBJECTS OF THE INVENTION

This invention, relates to a packaged synthetic absorbable suture having improved out of package handling characteristics and to a method of packaging polymeric articles having an inherent tendency to undergo degradation when exposed to water or a humid atmosphere, probably as a result of hydrolysis. More particularly, the invention is directed to improving the out of package flexibility and hand of synthetic absorbable sutures and to the packaging of articles and devices such as absorbable surgical sutures, clips, staples, implants, prostheses and the like, fabricated from polymers which are susceptible to hydrolytic degradation, notably, polymers and copolymers of glycolic acid (i.e., hydroxyacetic acid), the cyclic dimer of glycolic acid ("glycolide"), lactic acid, the cyclic dimer of lactic acid ("lactide") and related monomers, polydioxanone, polytrimethylene carbonate, polyalkylene glycol, polycaprolactone, their copolymers, etc. Polymers and copolymers of the foregoing kind and absorbable surgical devices made therefrom are well known. See, e.g. U.S. Pat. Nos. 2,668,162; 2,703,316; 2,758,987; 3,225,766; 3,297,033; 3,422,181; 3,531,561; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,060,089; 4,157,921; 4,157,437; 4,234,775; 4,237,920; 4,300,565; and 4,523,591; U.K. Patent No. 779,291; D. R. Gilding at al., "Biodegradable polymers for use in surgery—polyglycolic/poly(lactic acid homo- and co-polymers: 1, *Polymer*, Volume 20, pages 1459–1464 (1979), and D. F. William (ed.), *Biocompatibility of Clinical Implant Materials*, Vol. II, ch. 9: "Biodegradable Polymers" (1981). The biodegradability of these polymers/copolymers is believed to be due to the hydrolytic attack of their ester linkages by aqueous body fluids although the exact mechanism involved has been a matter of speculation. The present invention also extends to other surgical articles such as sutures based in whole or in part on a polyester polymer or copolymer such as polyglycolic acid, lactide-glycolide copolymer polydioxanone, polytrimethylene carbonate, polyalkylene glycols polycaprolactone, their copolymers etc.

Numerous patents, including U.S. Pat. Nos. 3,636,956; 3,728,639; 3,839,297; and 4,135,622 teach that synthetic absorbable surgical elements, particularly sutures, must be packaged and maintained under extremely dry conditions in order to be storage stable. Indeed, the preferred packaging and storage conditions described in the foregoing patents and used for commercially available synthetic absorbable sutures have a moisture level at or less than about 0.05% by weight of the suture, and preferably no more than about 0.02%. According to the patents, such conditions are attained by heating the suture and package to a high temperature under vacuum immediately prior to sealing, such as by heating to 180–188° F. for 1 hour under a 26 inch vacuum. U.S. Pat. Nos. 4,412,617 and 4,519,501 are consistent. The latter patents disclose a package for synthetic absorbable ligating clips packaged under the aforementioned extremely dry conditions and further including a pro-dried paper dessicant. In addition, synthetic absorbable staples and clips made primarily of lactide have been available for several years from U.S. Surgical Corporation, Norwalk, Conn. Such clips and staples are not as susceptible to hydrolysis as other commercially available absorbable surgical materials, and are not packaged under the very dry conditions described in any of the foregoing U.S. Patents, but rather are packaged in foil envelopes including a dessicant, such as a silica pouch. U.S. Pat. No. 3,382,141 discloses a dessicant paper.

Synthetic absorbable sutures typically are packaged in moisture impervious foil laminate envelopes with the suture wound in a so-called "figure 8" pattern on a paper card retainer. Typical retainers are shown in U.S. Pat. No. 4,249,656 entitled "Suture Package"; U.S. Pat. No. 4,253,563 entitled "Multistrand Suture Package"; and U.S. Pat. No. 4,0630638 entitled "Direct Dispensing Packaging of Surgical Sutures." Longer lengths of such sutures or ligatures are sold on a suture reel, such as disclosed in U.S. Pat. Nos. 3,648,949 and 3,749,238. Unfortunately, heretofore known synthetic absorbable sutures packaged under very dry conditions are relatively stiff and inflexible. Such sutures typically exhibit "memory" which causes the suture to retain and have a tendency to resume the figure 8 or coiled shape assumed by the packaged suture. The figure 8 configuration has also been found to introduce undesirable kinks and bends in the suture. These effects are highly undesirable since the suture must be straightened prior to use, and does not exhibit particularly good "feel" or "hand" characteristics important to the end user.

Molded suture packages having convoluted passageways are also known. By way of example, U.S. Pat. No. 3,338,401 entitled "Molded Suture Package" and U.S. Pat. No. 3,490,292 entitled "Method of Packaging Sutures" disclose a molded suture package wherein one or more elongated sutures are contained in a coiled narrow passageway having a plurality of convolutions. The foregoing patents teach that the suture may be drawn into the passageway by vacuum. The convoluted passageway desirably eliminates the introduction of kinks and bonds to the suture but, despite the desirable characteristics of molded suture packages, such packages have not been adopted for use in packaging synthetic absorbable sutures. It is speculated that the extremely dry conditions required for packaging prior synthetic absorbable sutures, together with the suture memory effect such very dry packaging conditions create, may combine to make it impossible to withdraw prior synthetic absorbable sutures from a molded suture package without breaking the suture.

Therefore, it would be highly desirable to provide a packaged synthetic absorbable suture having superior flexibility, "hand" and "feel" when removed from the package.

Accordingly, it is one object of the invention to provide a synthetic absorbable suture having improved out of package flexibility and hand.

It is a further object of the invention to provide a synthetic absorbable suture which does not exhibit undesirable memory effects.

Yet a further object of the invention is to provide a packaged synthetic absorbable suture which is more convenient to remove from the package.

Another object of the invention is to provide an improved package for sterile synthetic absorbable surgical elements.

Yet another object of the invention in to provide a packaged sterile synthetic surgical element which need not be packaged under extremely dry conditions.

These and other highly desirable and unusual results are accomplished by the present invention in a packaged synthetic absorbable suture which is amazingly supple, consistently easy to withdraw from the package, and, as removed from the package, does not exhibit memory or sets and has highly desirable out of package handling characteristics. The suture need, not be packaged under extremely dry conditions.

Objects and advantages of the invention am set forth in part herein and in part will be obvious herefrom or say be learned by practice with the invention, which is realized and attained by means of the instrumentalities and combinations pointed out in the appended claims.

The invention consists of the novel parts, constructions, arrangements, combinations, steps, and improvements herein shown and described.

SUMMARY OF THE INVENTION

The present invention provides a sterile packaged synthetic absorbable suture filled with a stabilizing agent, preferably a mixture of glycerol and calcium lactate, packaged in a suture retainer disposed within a substantially moisture impervious foil pouch. The preferred retainer is a molded retainer having at least one convoluted passageway, with one or more sutures disposed in the passageway. The preferred pouch is a peelable fail pouch. The preferred suture is a braided suture made from a glycolide-lactide copolymer having a particular braid configuration and filled with a stabilizing agent such as glycerol. In the preferred embodiment the stabilizing agent further includes a thickener, such as calcium lactate. Contrary to prior practice, the sterile synthetic absorbable sutures prepared and packaged in accordance with the invention need not be packaged under the extremely dry conditions required by prior packaged synthetic absorbable suture and are preferably packaged having a moisture level above about 0.2% by weight of the filled, braided suture. It is further preferred that the moisture level be above about 0.5% by weight of the suture. Indeed, the very dry packaging conditions of prior synthetic absorbable sutures would be deleterious to the packaged sutures of the present invention. The preferred package further includes a package stabilizing element for maintaining the moisture level within the package and suture within a very close range of its initial, relatively high, level and for preventing migration of the suture filling to surrounding package materials. Uniformity of the moisture level and suture filling contributes to consistent force to withdraw the suture from the package, and to the highly desirable out of package handling characteristics of filled braided sutures. By way of example only, the package stabilizing element may consist of a sheet of paper filled with the same stabilizing agent used to fill the sutures.

The braided filled synthetic absorbable suture packaged in accordance with the invention resists kinks and bonds introduced by prior packaging conditions and materials so as to provide a synthetic absorbable suture having remarkable handling characteristics i.e. "band" and "feel" upon removal of the suture from the package. Indeed, the preferred braided filled synthetic absorbable sutures packaged in accordance with the invention have favorable out of package vertical hanging length, bond length and Gurley stiffness characteristics. That is, upon removal from the package the sutures have a straight vertical hanging length of about 80% of their straightened length, a bending length of about 3.0 and a Gurley stiffness less than about 5.0. In qualitative terms, the packaged synthetic absorbable sutures in accordance with the present invention have remarkable out of package hand and feel comparable to commercially available braided silk sutures. Such handling characteristics for braided synthetic absorbable sutures are unheard of and simply amazing.

In accordance with the method of the present invention, synthetic absorbable sutures filled with a stabilizing agent, such as a mixture of glycerol and calcium lactate, are loaded into a retainer which in then placed in an open foil pouch, sterilized, equilibrated and sealed. Preferably, the sutures are braided sutures composed primarily of glycolide, such as a copolymer of about 90% glycolide and 10% lactide. The preferred retainer is a molded retainer having at least one convoluted passage, with the suture being drawn into the molded Passageway under vacuum leaving one and of the suture, which may be needled or non-needled, protruding from the passageway. The suture and retainer are placed into an open foil laminate envelope, which is preferably a peelable foil pouch. In a further embodiment of the invention, a package stabilizing element, which may consist of a paper shoot filled with the same stabilizing agent used to fill the sutures, is also inserted into the foil laminate envelops. The suture in the unsealed foil laminate envelope is sterilized, such as by treatment in an ethylene oxide gas sterilization cycle with subsequent aeration to remove residual ethylene oxide, all in a known manner. The sterile surgical elements are then equilibrated, such as in a dew point controlled environment, until the desired moisture level is attained. The moisture level should be far above the very dry conditions under which commercially available synthetic absorbable sutures have heretofore been packaged, since such very dry conditions are deleterious to the filled braided sutures. The moisture level should exceed about 0.2% by weight of the suture and is preferably above about 0.5%. The equilibrated suture package is then sealed and placed into inventory. The suture is removed from the package by opening the foil pouch, such an by peeling open the preferred peelable pouch, grasping the end of the suture protruding from the passageway, and withdrawing the suture from the retainer. In the case of the preferred molded retainer, withdrawing the suture by pulling the suture through the convoluted passageway has the desirable effect of flexing the suture, further improving the out of package characteristics of the suture.

The preferred braided filled suture packaged in accordance with the invention results in a packaged synthetic absorbable suture having amazing flexibility and suppleness upon removal from the package. As stated, the filled sutures advantageously are packaged at a relatively high moisture level, higher than could be tolerated by prior synthetic absorbable sutures. The relatively high moisture level simplifies manufacturing processes and permits use of a molded retainer to assume that the suture is and remains free from kink and bends introduced by prior packaging techniques. The high moisture level and molded retainer contribute to the ease with which the filled suture may be withdrawn from the suture package and the desirable out of package characteristics of such sutures. The package stabilizing element maintains the moisture level in the envelope within a preset range and prevents undue change, whether increased or decreased, thereby contributing to the stability of the filling composition and consistent force to remove the filled suture from the molded suture retainer, It has also been found that the suture of the invention may be impregnated with one or more medico-surgically useful substances, such as therapeutic agents or Human growth Factors. Advantageously, it has been found that the preferred filling composition is an appropriate carrier for Human Growth Factors and that Human Growth Factors impregnated into the suture in the filling composition remain active even after sterilization.

It will readily be appreciated that the aforementioned objects and advantage, among others, have been achieved with the suture and package of the present invention. Thus, the present invention provides a packaged synthetic absorbable suture having improved handling characteristics which need not be packaged under extremely dry conditions and which may advantageously be packaged in a molded suture retainer. The braided, filled suture packaged in accordance with the invention consistently provides heretofore unknown convenience in removal of the suture from the package and the suture, as removed from the package, exhibits amazing flexibility and suppleness without undesirable bonds, kinks or memory effects commonly associated with prior packaged synthetic absorbable sutures.

It will be understood that the foregoing general description and the following detailed description as well are exemplary and explanatory of the invention but are not restrictive thereof.

The term "filled" as used herein refers to the association of the polymeric article with a storage stabilizing amount of storage stabilizing agent, whether this Association be one in which the storage stabilizing agent is absorbed by the polymeric article, in present on the surfaces thereof or is a combination of the two.

The term "stabilizing agent" as used herein refers to a material which, when associated, such an by filling, with a polymeric article susceptible to hydrolysis, improves the storage stability of the polymeric article and eliminates any need to store the article in an artificially-maintained very dry environment.

The term "package stabilizing element" as used herein refers to a material which maintains the stabilizing agent solvent level within a sealed package against any substantial increase or decrease, and specifically includes but is not limited to a mass of stabilizing agent within the package separate and apart from a filled polymeric article. In the context of the preferred embodiment of the invention water is the stabilizing agent solvent, and the package stabilizing element will hereinafter be discussed in the context of water based systems, but should not be construed to be limited thereto.

The term "braid" or "braided" as applied to the suture of this invention refers to an arrangement of discrete units, or bundles, denominated "sheath yarns", made up of individual filaments with individual sheath yarns interlocking or interlacing each other in a regular criss-cross pattern. Although preferred braid structures are disclosed and discussed herein, the terms "braid" or "braided" as used herein should not be considered to be limited to such structures, and includes other braid structures, whether or not including a care, and spiroid braids.

The term "pick count" refers to the number of crossovers of sheath yarns per linear inch of suture and, together with the overall denier of the suture, the denier of the individual filaments constituting a sheath yarn and the number of sheath yarns employed defines the principal construction characteristics of the preferred braided suture herein.

The term "standard suture" is intended to designate any of the heretofore known braided sutures, e.g., those described in U.S. Pat. No. 3,565,077, and in particular, braided suture products marketed by Ethicon, Inc. under its Vicryl brand and those marketed by Davis & Geck, Inc. (American Cyanamid Co.) under its Dexon brand.

BRIEF DESCRIPTION OF THE DRAWINGS

The accompanying drawings, referred to herein and constituting a part hereof, illustrate the preferred embodiments of the product and method of the present invention, and together with the description serve to explain the principles of the invention, in which.

DETAILED DESCRIPTION OF THE PREFERRED EMBODIMENTS

The preferred embodiment of the invention is directed to a package and method for braided synthetic absorbable sutures which results in a packaged synthetic absorbable suture having very desirable out of package handling characteristics. The preferred package is a peelable foil housing a retainer, preferably a molded retainer having at least one narrow convoluted passageway, containing at least one braided synthetic absorbable suture filled with an appropriate stabilizing agent. As described in greater detail below, the preferred stabilizing agent is glycerol containing a thickener, such as calcium lactate. The presence of the stabilizing agent permits the suture to be packaged at a relatively high moisture level, which eliminates any need for extreme measures to ensure very dry conditions in the package. The combined effects of the stabilizing agent and high moisture level advantageously permit the suture to be packaged in and removable from a molded suture retainer in order to preserve the desirable hand and feel of the filled suture. The preferred embodiment further includes a package stabilizing element, such as a paper sheet filled with stabilizing agent, for maintaining the moisture level within the package and preventing migration of the stabilizing agent from the suture to surrounding package materials. Maintaining the moisture level within a close range also assures uniform force to withdraw the suture from the retainer. The braided, filled suture, as removed from the package, exhibits very desirable handling characteristics which may be expressed in terms of out of package hanging length, banding length and Gurley stiffness.

Figure 1:
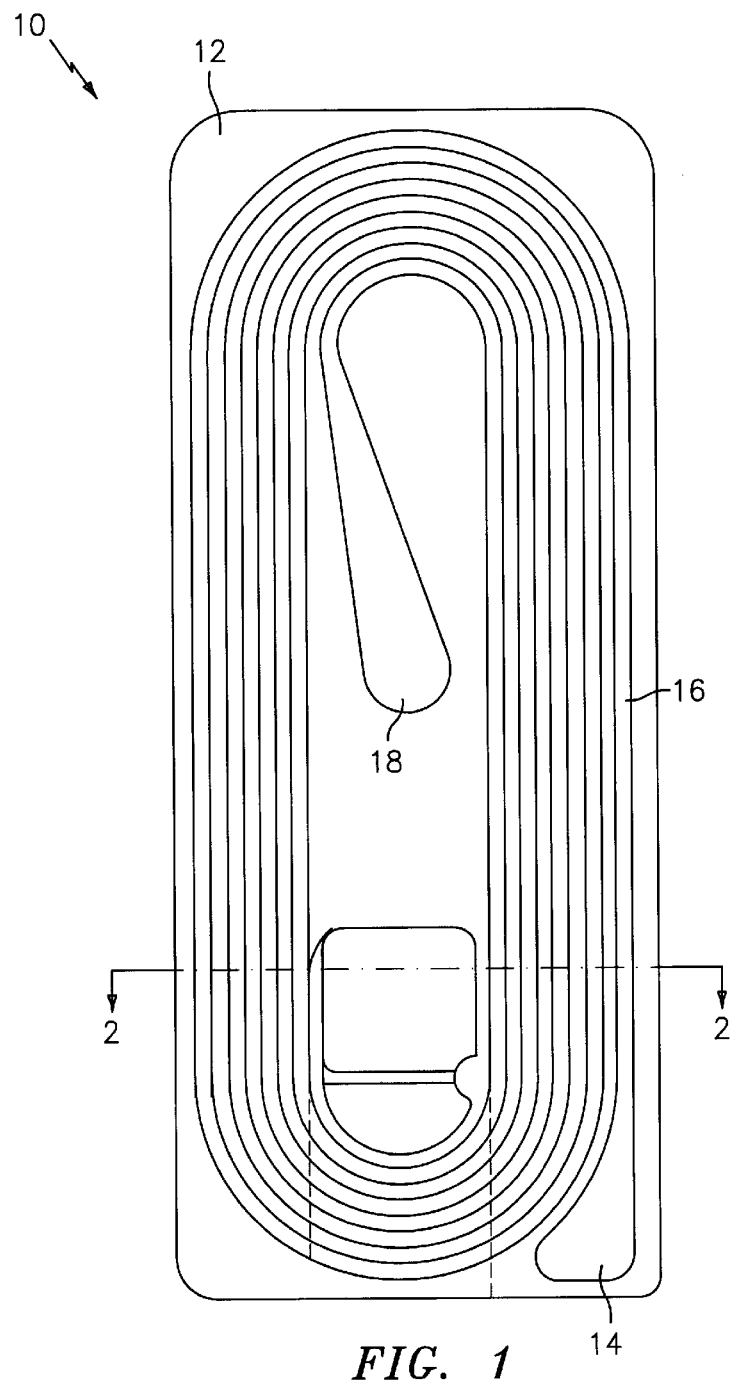
FIG. 1 is a plan view of a first suture retainer embodiment.
Figure 2:
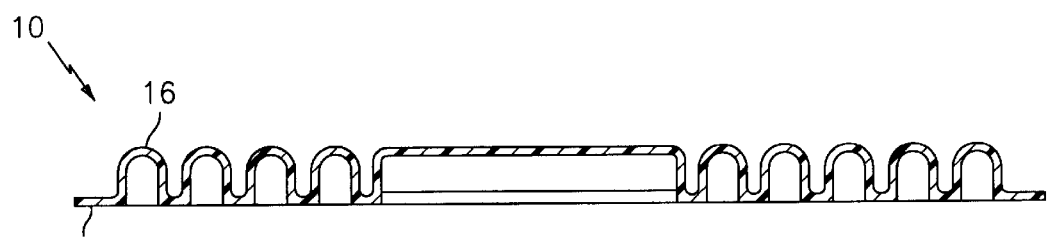
FIG. 2 is a cross-section view of the retainer of FIG. 1 taken along lines 2—2.

Referring now to FIG. 1, there is shown a plan view of a molded suture retainer 10 in accordance with the invention. The molded suture retainer illustrated in FIG. 1 finds particular application for holding full length single sutures up to about thirty inches in length. As shown, retainer 10 has a base 12 and an enlarges suture receiving section 14 leading to a convoluted narrow passageway 16. The convoluted narrow passageway follows a spiral oval pattern through several turns and terminates at a central vacuum receiving section 18. FIG. 2 is a cross-section view of the retainer shown in FIG. 1 taken along lines 2—2 of FIG. 1, illustrating base 12 with molded passageway 16 extending from the base. Preferably, base 12 is approximately 3.355 inches (85.217 millimeters) by 1.375 inches (34.925 millimeters) in order to conform to commonly accepted overall dimensions of conventional suture packages and display boxes. Of course, these dimensions require several convolutions of the narrow passageway in order to accomodate any appreciable suture length. It is believed that the number of curved surfaces created by such convolutions may be a contributing cause to the prior inability to package synthetic absorbable sutures in a molded suture package having convoluted passageways. That is, the suture wrapped around the curved surfaces of the convolutions creates a capstan effect which is exacerbated by the very dry package conditions such prior sutures require. The retainer of FIGS. 1 and 2 may be molded so that the convoluted passageway has a depth of approximately 0.070 inches (1.778 millimeters) and a width of approximately 0.047 inches (1.194 millimeters).

Preferably, the molded suture retainer is made from polyethylene teraphthalate (PETG), such as Eastman Kodak 6763.

Figure 3:
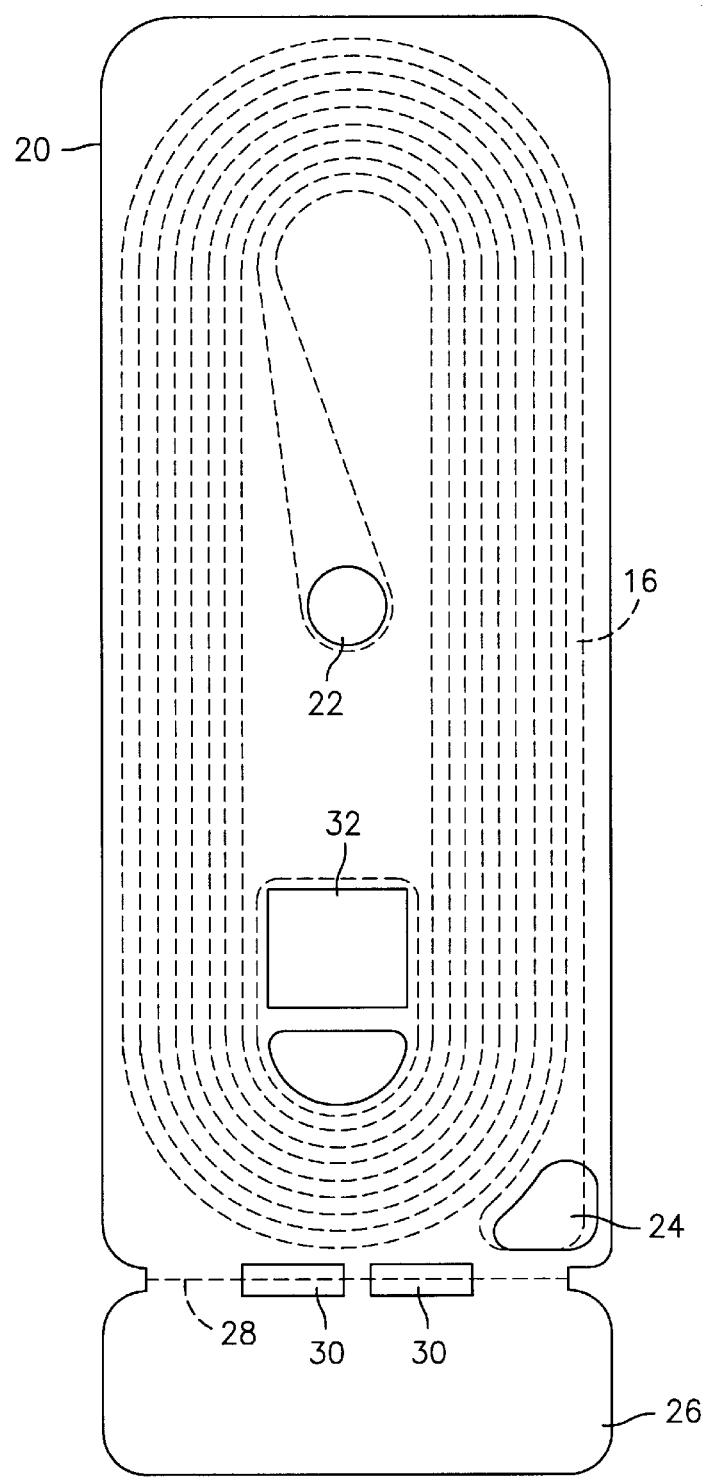
FIG. 3 is a plan view of a cover sheet for the suture retainers of FIGS. 1–2 and 4–7.

Referring now to FIG. 3, there is shown an appropriate cover sheet 20 for the retainer shown in FIGS. 1 and 2. Cover sheet 20 is configured and dimensioned to overlie the open top of the retainer, and is provided with a vacuum aperture 22 and a suture entrance aperture 24. Cover sheet 20 is adhesively attached to the molded retainer and covers the convoluted passageway. Vacuum aperture 22 aligns and communicates with central vacuum receiving section 18 of the molded retainer. Similarly, suture entrance aperture 24 aligns and communicates with enlarged suture receiving section 14. Preferably, cover sheet 20 is constructed of a material which is pervious to ethylene oxide sterilizing gas and which does not have a high affinity for suture filling materials such as glycerol. The preferred material is a spun bonded polyolefin, such as Tyvek 1073B available from E. I. DuPont de Nemours & Co. As stated, the cover sheet is adhesively attached to the molded retainer. In the preferred embodiment the cover sheet is adhered to the retainer with a hot melt adhesive, such as Oliver 18B adhesive coating available from Oliver Products of Minneapolis, Minn. While not believed to be critical to the present invention, other combinations of cover sheet and adhesive have been found ineffective for various reasons, such as failure of the adhesive to hold after sterilization. As shown, cover sheet 20 preferably includes a fold-over panel 26 joined to the main section of the cover sheet at a perforate score line 28 with openings 30. The cover sheet also preferably has a foam needle park 32 for holding a needle in place. In FIG. 3 convoluted passageway 16 is shown in phantom to illustrate the relationship of the cover sheet to the molded retainer.

As a practical matter, it becomes difficult to form a passageway in excess of thirty inches in the surface area permitted by commonly accepted suture package dimensions. Even if such a retainer can reliably be formed, the inner spiral develops a very tight radius which increases the capstan effect, and, consequently, the force to withdraw longer length sutures from the retainer. Therefore, it is contemplated that, in order to provide optimum suture pull out force, it may be desirable to package in full length configuration only sutures having lengths less than thirty and preferably less than about twenty seven inches. It is also contemplated that multiple lengths may be packaged in one retainer, and that longer lengths of sutures may be packaged doubled or tripled over so as to obtain a shorter overall effective suture length to be withdrawn from the retainer. In the case of the latter multiply packed or doubled or tripled over sutures, modified retainers are contemplated.

Figure 4:
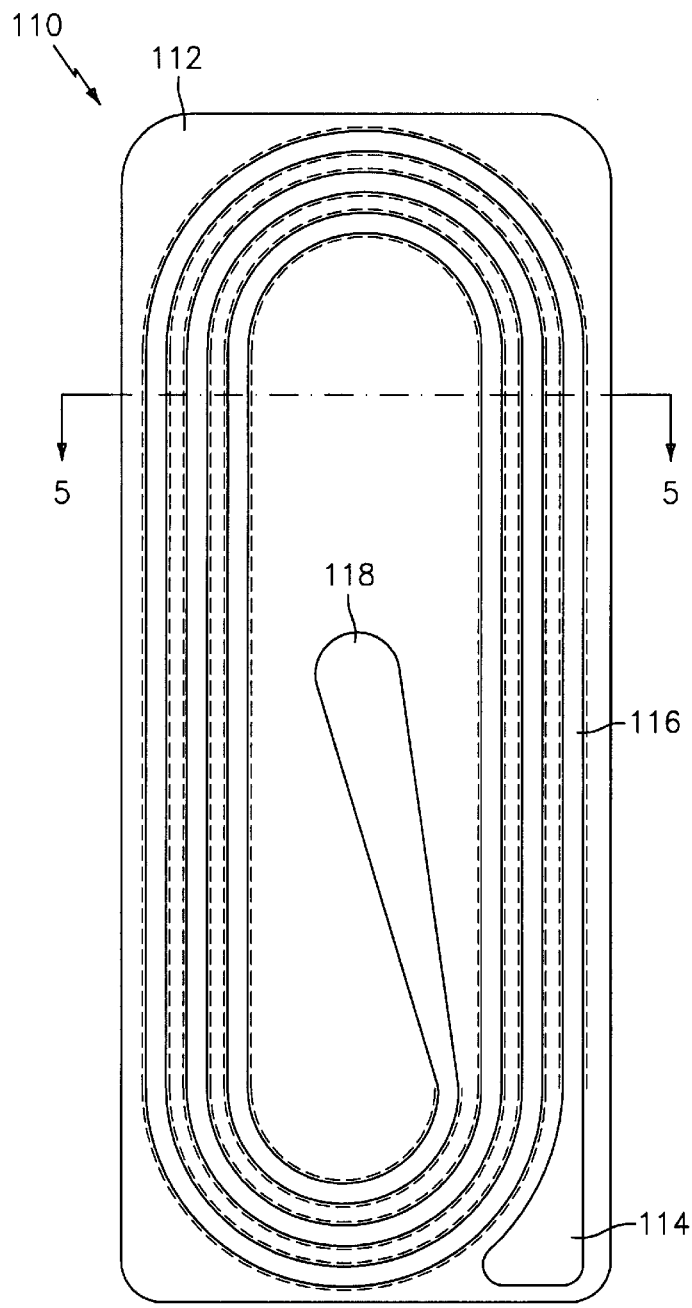
FIG. 4 is a plan view of a second suture retainer embodiment.
Figure 5:
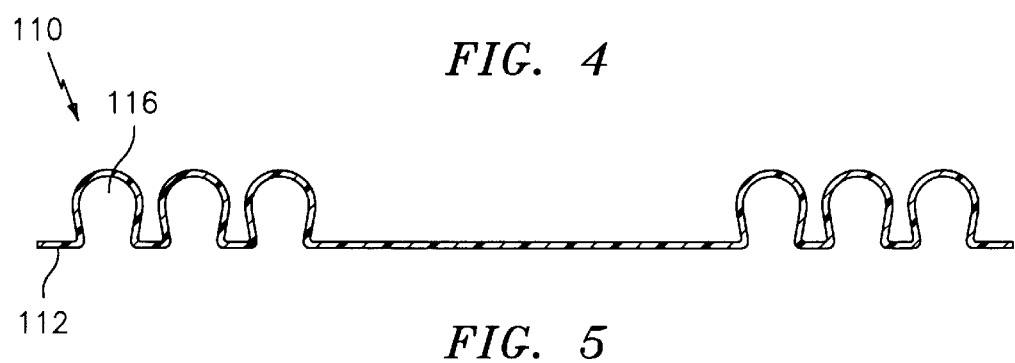
FIG. 5 is a cross-section view of the retainer of FIG. 4 taken along lines 5—5 of FIG. 4.

Referring now to FIGS. 4 and 5, there is shown a first alternative retainer configured and dimensioned to receive and hold multiple full length sutures. Referring to FIG. 4, the retainer 110 has a base 112 having an overall length of approximately 3.355 inches (85.217 millimeters) and a width of approximately 3.375 inches (34.925 millimeters). Base 112 has an enlarged suture receiving section 114, a convoluted narrow passageway 116, and a central vacuum receiving section 118. The cover sheet 20 illustrated in FIG. 3 may be adhered to retainer 110 in the same manner as described with respect to retainer 10. Referring to FIG. 5, a cross-section view of retainer 110 along lines 5—5 of FIG. 4, narrow passageway 116 preferably is molded to have a depth of approximately 0.100 inches (2.540 millimeters) and a width of approximately 0.078 inches (1.984 millimeters). The retainer of FIGS. 4 and 5 is particularly suited for receiving and holding as many as about five full length suture strands up to about twenty seven or thirty inches in length. Preferably, the suture strands are simultaneously loaded into the retainer.

Figure 6:
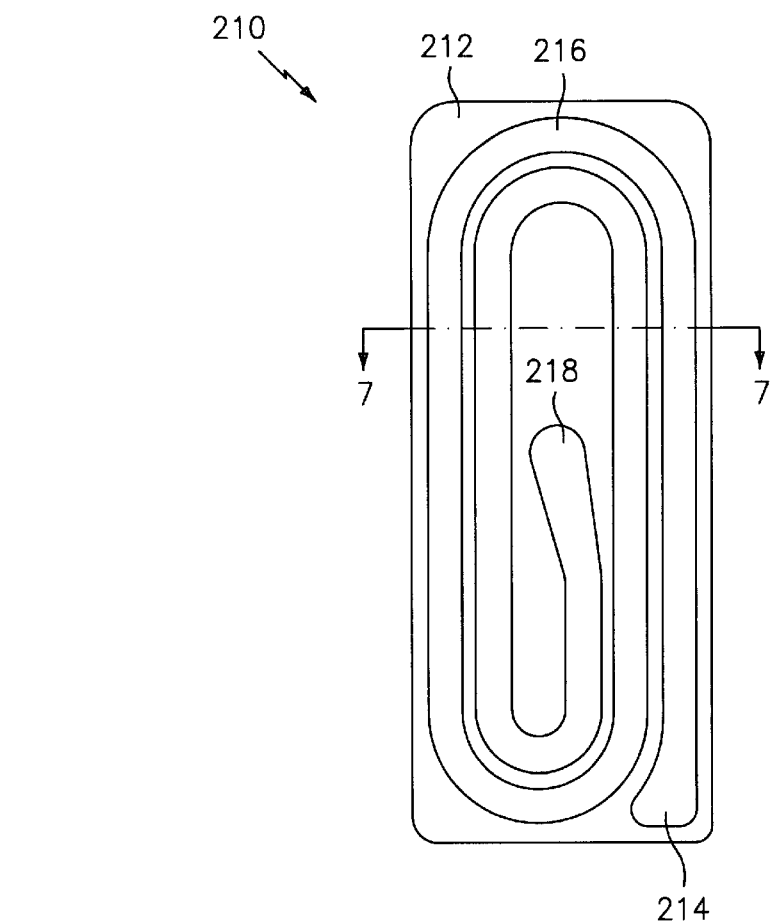
FIG. 6 is a plan view of a third suture retainer embodiment.
Figure 7:
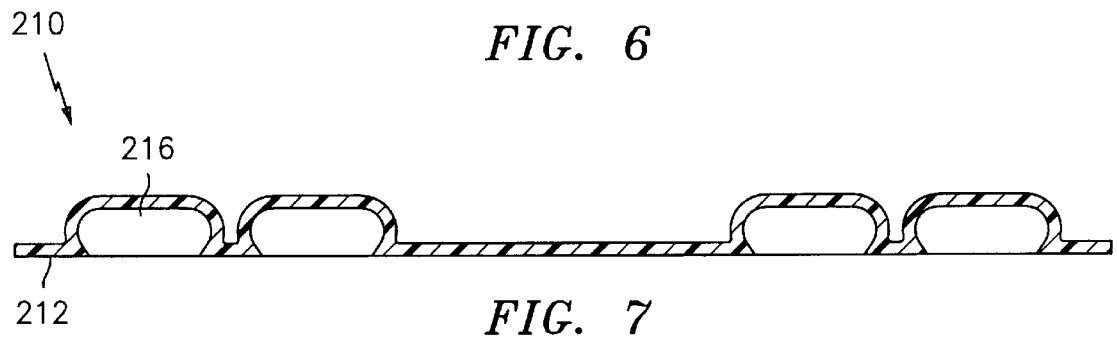
FIG. 7 is a cross-section view of the retainer of FIG. 6 taken along lines 7—7 of FIG. 6.

In a second alternative embodiment illustrated in FIGS. 6 and 7, a much wider passageway having fewer convolutions is provided. The retainer 210 has a base 212 which is substantially the same size as the aforementioned retainers, approximately 3.350 inches (85.09 millimeters) by 1.375 inches (34.925 millimeters). Passageway 216 is substantially wider than prior embodiments, and preferably is about 0.060 inches (1.524 millimeters) deep and 0.200 inches (5.080 millimeters) wide (see FIG. 7). Passageway 216 communicates with an enlarged suture receiving section 214 and a central vacuum receiving section 218. As in the prior embodiments, cover sheet 20 (see FIG. 3) is attached to retainer 210 by a hot melt adhesive such that vacuum aperture 22 aligns with vacuum receiving section 218 and suture entrance aperture 24 aligns with enlarged suture receiving section 214. Retainer 210 is well suited for packaging doubled over sutures, such as double armed sutures, and is preferred for longer lengths of suture, i.e. in excess of thirty inches, packaged in a tripled over configuration.

Figure 8:
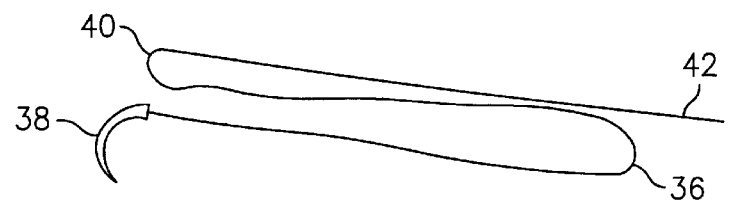
FIG. 8 is an illustration of a tripled-over suture.

Referring to FIG. 8, in order to load a tripled over suture into the retainer of FIGS. 6 and 7, a suture 34, such as a suture which exceeds thirty or even thirty six inches in length, is looped to form a first curved portion or half loop 36 distal to the needle 38 and a second curved portion or half loop 40 adjacent the needle. A suture tail end 42 extends beyond the first half loop 36, preferably by at least about one inch. With vacuum applied to the retainer, such as by placing a vacuum block over vacuum aperture 22 (see FIG. 3), suture tail end 42 and then first half loop 36 are sequentially inserted through suture entrance aperture 24 into passageway 216, while holding the suture adjacent the needle and the second loop. The suture is drawn into the retainer by vacuum until the needle is disposed adjacent suture aperture 24 and may be mounted in needle park 32. It is important that suture tail end 42 extend beyond the first half loop at all times so that a knot is not inadvertently formed in the suture during insertion or removal from the retainer.

As in the case of the first molded retainer embodiment, the retainers shown in FIGS. 4 through 7 may be molded of polyethylene teraphthalate, (PETG) such as Eastman Kodak 6763. In all cases, the retainers should be about 0.010 inches (0.254 millimeters) thick.

Figure 9:
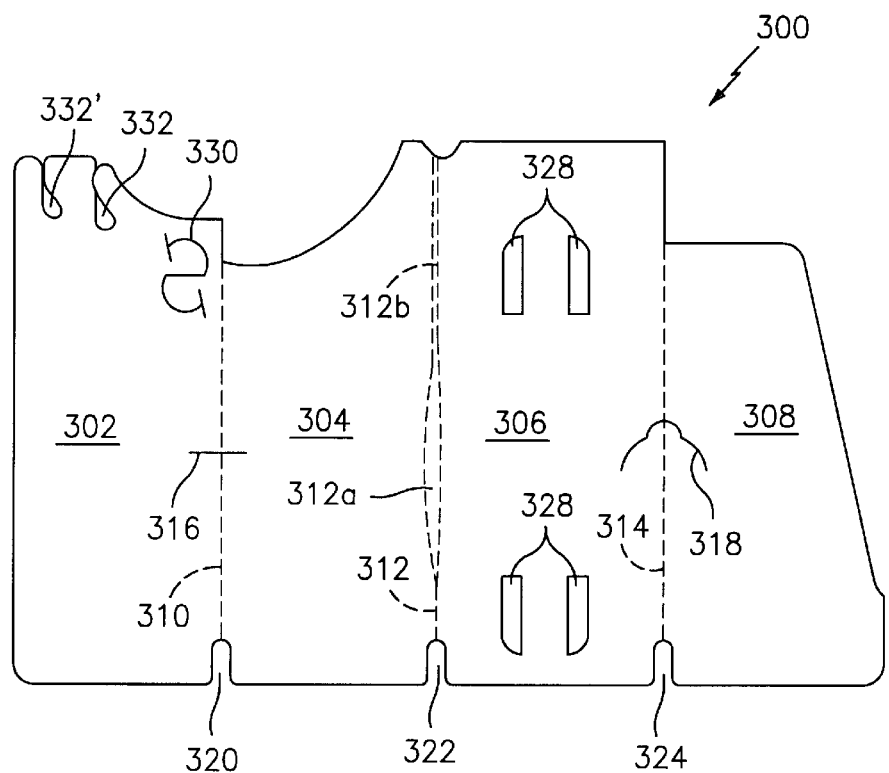
FIGS. 9 and 10 are plan views of an alternative suture retainer in the fully unfolded and fully folded conditions, respectively.
Figure 10:
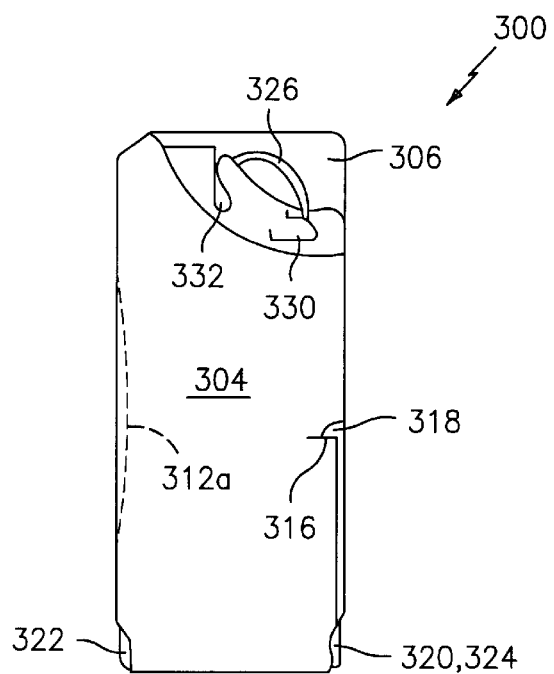

Although not preferred, it is contemplated that other types of suture retainers could be used in packaging the preferred braided filled sutures to obtain improved out of package handling characteristics, although not necessarily as remarkable as the results obtained with the molded retainer. By way of example only, a suitable four panel suture retainer card is shown in FIGS. 9–10. FIG. 9 illustrates a fully unfolded surgical suture retainer card member 300 which can also be used in the package of this invention and FIG. 10 illustrates retainer 300 in the fully folded condition which it assumes when loaded and ready to be inserted within the packet of the foil pouch.

Retainer member 300 is made up of four panels, namely, needle retaining panel 302, front cover panel 304, suture winding panel 306 (which also functions as the rear panel of the fully folded retainer) and fold-over panel 308. Retainer member 300 is preferably formed from a single sheet of suitable material, e.g., stiff paper or paperboard such as 5 point to 12 point solid, bleached sulfate board, plastics, foils, laminates, and the like, which is die cut to provide the desired configuration. The panels are joined to each other along perforate, or score, lines 310, 312 and 314 which facilitate their folding and central gusset sections 312a and 312b provide a space or clearance between panels 304 and 306. Die cut 316 cooperates with die cut 318 to provide a snap-lock feature which maintains the retainer in the fully folded condition. Rounded indentations 320, 322 and 324 serve to prevent the suture from becoming caught between the panels when folded.

To load needle 326 with its attached suture (not visible) into retainer 300, the retainer is first secured in place by means of loading pins (not shown) which project through openings 328 in panel 306. The point of needle 326 is then inserted in die cut 330 which is shaped somewhat like a reversed "S" by threading the point under the upper, and then over the lower, half of the reversed "S" cut and then behind panel 302 so that the needle shack and tip are on opposite sides of panel 302. Slight tension is maintained on the suture from this stage of the loading procedure to the conslusion of the procedure to ensure that needle 326 will maintain its placement in die cut 330 as previously described. The shank of needle 326 is then threaded through one of teardrop-shaped cutouts 332 or 332', cutout 332 being used for smaller needles (as shown in FIG. 10) and cutout 332' being used for larger needles. After panel 302 has been folded over onto panel 304, the suture is wound figure "8" pattern around the loading pins projecting through openings 328 in panel 306. Retainer 300, now loaded with needle 326 and the attached suture, is released from the loading pins, panel 308 is folded over on panel 306 and the partly folded-over structure is given a final folding along perforate line 312 and gussets 312a and 312b. Finally, a slight counter-directional movement of the upper section of the retainer against its lower section sets the aforementioned snap-lock in place providing the fully assembled, loaded retainer of FIG. 10.

All of the retainers illustrated in FIGS. 1–7, 9 and 10 are preferably packaged in the pealable pouch disclosed in co-pending U.S. patent application Ser. No. 07-388,152, the entire contents of which are incorporated by reference.

Figure 11:
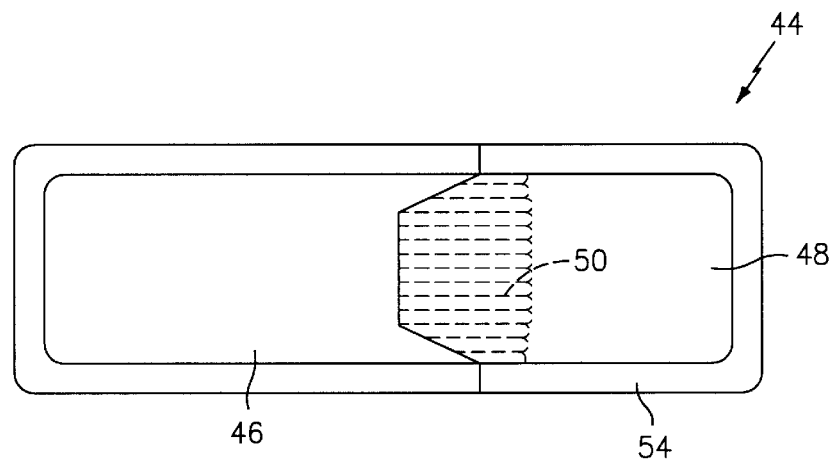
FIG. 11 is a plan view of the preferred peelable pouch in a closed position.
Figure 12:
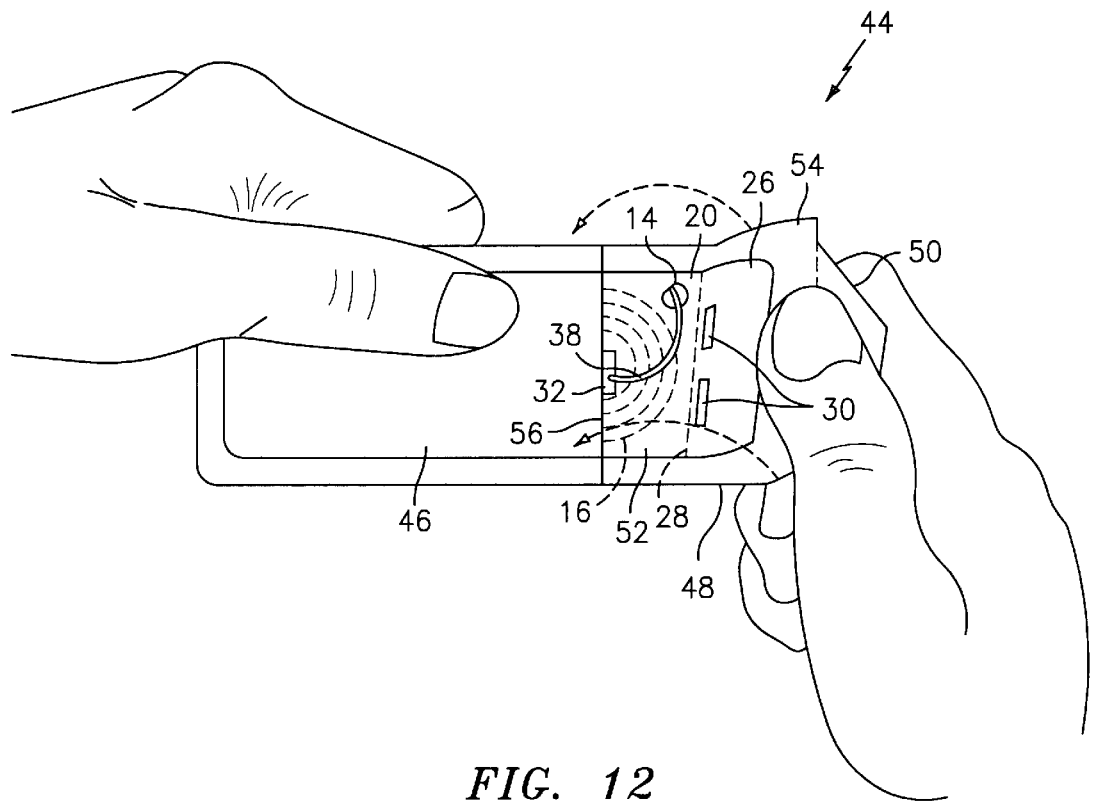
FIG. 12 is a plan view of a partially open peelable pouch.

The preferred peelable pouch is shown in FIGS. 11 and 12. FIG. 11 is a top plan view of the preferred peelable pouch in the closed position, and FIG. 12 illustrated the pouch partially peeled open. The peelable pouch 44 has a top layer comprised of first and second top panels 46, 48, respectively. The first and second top panels are adhered to each other transversely across the pouch, leaving a gripping tab 50. The top panels are adhered to a bottom panel 52 at a peripheral seal 54, i.e. at the transverse and longitudinal edges of the pouch or envelope, so as to define a pocket for receiving a suture retainer. As shown in FIG. 12, first top panel 46 dose not extend the full length of bottom panel 52, but terminates at a first top panel transverse edge 56. Upon peeling the pouch open, needle 38 is seen protruding from suture aperture 14 in cover sheet 20 and is held in position by needle park 32. The needle is plainly visible and accessible for removal of the suture from passageway 16 (shown in phantom) in the retainer. Preferably, fold over panel 26 is adhered to second top panel 48, so that upon opening the peelable pouch the needle is revealed and accessible. Top panels 46, 48 and bottom panel 52 may be constructed of a foil laminate material with a hot melt adhesive on the inner surface of each panel for forming peripheral seal 54 and the seal between the overlapping first and second top layer panels. The foregoing peelable pouch is preferred, but it will be understood that other types of envelopes, such as conventional tearable foil laminate envelopes, can be used. See, for example, U.S. Pat. Nos. 3,939,969 and 4,014,433. It is contemplated that the suture could be sterilized by ethylene oxide permeating through an opening in the peelable pouch which is subsequently sealed, and that the peelable pouch itself should be sterilized and maintained sterile in an outer breather pouch in a known manner. See, for example, U.S. Pat. Nos. 3,815,315 and 4,603,538.

The suture can be monofilament or braided, and preferably is a braided suture made from a copolymer fabricated from any suitable bioabsorbable polymer. The polymer may be derived at least in part from glycolic acid, glycolide, lactic acid or lactide, and preferably is a copolymer of about 90% mol. weight glycolide and 10% mol. weight lactide. The preferred braided suture is constructed in accordance with U.S. patent application Ser. Nos. 07-089,732, 07-227,699; 07-344,745; and 07-491,215, the entire contents of which are hereby incorporated by reference. Thus, for a suture braid construction for a given range of overall suture denier, the range of pick count, number of sheath yarns and denier of individual filaments comprising a sheath yarn preferably are related to each other as set out in Table I. Individual filament denier can vary in weight from about 0.2 to about 6.0 denier. Preferred ranges are set out in Table I.

TABLE I

SUTURE BRAID CONSTRUCTION

| Suture Size | Overall Suture Denier | Pick Count | Number of Sheath Yarns | Denier of Individual Filaments |
|---|---|---|---|---|
| 7/0, 8/0 | from about 50 to about 125 | from about 50 to about 100, and preferably from about 55 to about 80 | from about 4 to about 16, and preferably from about 6 to about 14 | from about 0,2 to about 1.8, and preferably from about 0.8 to about 1.4 |
| 6/0 | greater than about 125 to about 200 | from about 50 to about 100, and preferably from about 55 to about 80 | from about 4 to about 16, and preferably from about 6 to about 14 | from about 0.2 to about 1.8, and preferably from about 0.8 to about 1.4 |
| 5/0 | greater than about 200 to about 300 | from about 50 to about 100, and preferably from about 55 to about 80 | from about 4 to about 16, and preferably from about 6 to about 14 | from about 0.2 to about 1.8, and preferably from about 0.8 to about 1.4 |
| 4/0 | greater than about 300 to about 500 | from about 150 to about 100, and preferably from about 55 to about 80 | from about 10 to about 20, and preferably from about 12 to about 14 | from about 0.2 to about 1.8, and preferably from about 0.8 to about 1.4 |
| 3/0 | greater than about 500 to about 800 | from about 50 to about 100, and preferably from about 55 to about 80 | from about 14 to about 20, and preferably from about 14 to about 18 | from about 0.2 to about 1.8, and preferably from about 0.8 to about 1.4 |
| 2/0 | greater than about 800 to about 1200 | from about 50 to about 100, and preferably from about 55 to about 80 | from about 16 to about 32, and preferably from about 20 to about 30 | from about 0.2 to about 1.8, and preferably from about 0.8 to about 1.4 |
| 0 | greater than about 1200 to about 2000 | from about 50 to about 100, and preferably | from about 20 to about 36, and preferably | from about 0.2 to about 1.8, and preferably |
| 1,2 | greater than about 2000 to about 4000 | from about 50 to about 100, and preferably from about 55 to about 80 | from about 24 to about 34, and preferably from about 24 to about 34 | from about 0.6 to about 1.4 from about 0.2 to about 1.8, and preferably from about 0.8 to about 1.4 |

For some suture braids, it may be desirable to include a core in the braid structure. Preferred core denier for a given suture having an overall suture denier are set out in Table II.

TABLE II

SUTURE CORE DENIER

| Suture Size | Overall Suture Denier | Denier of Core |
|---|---|---|
| 6/0 | greater than about 125 to about 200 | from about 20 to about 80, and preferably from about 25 to about 50 |
| 5/0 | greater than about 200 to about 300 | from about 30 to about 100, and preferably from about 50 to about 80 |
| 4/0 | greater than about 300 to about 500 | from about 80 to about 150, and preferably from about 80 to about 120 |
| 3/0 | greater than about 500 to about 800 | from about 150 to about 300, and preferably from about 180 to about 280 |
| 2/0 | greater than about 800 to about 1200 | from about 250 to about 700, and preferably from about 350 to about 650 |
| 0 | greater than about 1200 to about 2000 | from about 400 to about 1200, and preferably from about 500 to 1000. |
| 1,2 | greater than about 2000 to about 4000 | from about 800 to about 2400, and preferably from about 1000 to about 2200 |

Parent U.S. patent application Ser. No. 07-089,735, filed Aug. 26, 1987, the entire contents of which are incorporated herein by reference, discloses a method for improving the storage stability of a polymeric article susceptible to hydrolysis which comprises applying a storage stabilizing amount of at least one water soluble hygroscopic polyhydroxy compound or ester thereof to the polymeric article as a storage stabilizing agent therefor. Such method does not require the article to be subjected to extreme drying steps prior to completion of the packaging operation, as must be done with prior synthetic absorbable sutures. In order to avoid migration of the hydroscopic polyhydroxy compound or ester thereof from the polymeric surgical article to the surrounding packaging material, parent U.S. patent application Ser. No. 07-221,308, filed Jul. 19, 1988, the entire contents of which are incorporated herein by reference, discloses and claims a method for improving the storage stability of a polymeric article susceptible to hydrolysis which comprises applying a storage stabilizing amount of a mixture of at least one water soluble hygroscopic polyhydroxy compound or ester thereof and a thickening compound. Many kinds of pharmaceutically acceptable non-aqueous thickeners can be utilized including water-soluble polysaccharides, e.g., hydroxypropyl methylcellulose (HPMC), and the other materials of this type which are disclosed in European Patent Application 0 267 015, polysaccharide gums such as guar, xanthan, and the like, gelatin, collagen, etc. An especially preferred class of thickeners are the saturated aliphatic hydroxycarboxylic acids of up to 6 carbon atoms and the alkali metal and alkaline earth metal salts and hydrates thereof. Within this preferred class of compounds are those of the general formula

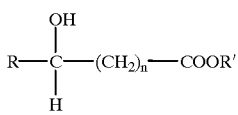
(I)

wherein R is hydrogen or methyl, R' is alkali metal or alkaline earth metal, and n is 0 or 1 and hydrates thereof.

Preferably, the components which make up the stabilizing agent of the present invention have no appreciable toxicity for the body at the levels present. With these requirements in mind, those skilled in the art are readily capable of identifying any number of compounds which may be useful in the practice of this invention. Among the specific water-soluble hydroscopic polyhydroxy compounds or esters thereof which can be used herein with generally good results are glycerol and its mono- and diesters derived from low molecular weight carboxylic acids, e.g., monoacetin and diacetin (respectively, glyceryl monoacetate and glyceryl diacetate), ethylene glycol, diethylene glycol, triethylene glycol, 1,3-propanediol, trimethylolethane, trimethylolpropane, pentaerythritol, sorbitol, and the like. Glycerol is especially preferred. Mixtures of the aforediscussed polyhydroxy compounds or esters, e.g., sorbitol dissolved in glycerol, glycerol combined with monoacetin and/or diacetin, etc., are also useful. Compounds within the general formula (I), above, useful in formulating the stabilizing agent mixture of the present invention include, for example, salts of lactic acid such as calcium lactate, potassium lactate, sodium lactate, salts of glycolic acid, such as calcium glycolate, potassium glycolate, sodium glycolate, salts of 3-hydroxy propanoic acid, such as the calcium, potassium and sodium salts thereof, salts of 3-hydroxybutanoic acid, such as the calcium, potassium and sodium salts thereof and the like. As stated hereinbefore, hydrates of the compounds within the scope of the general formula (I) hereinabove are also within the scope of the present invention. Calcium lactate, especially calcium lactate pentahydrate, is a particularly preferred thickener. Where a thickener is utilized, it will be incorporated in the filling composition in at least that amount required to increase the overall viscosity of the composition to the point where the composition no longer readily drains away from the suture in a relatively short period.

If necessary or desirable, the stabilizing agent can be dissolved in any suitable non-aqueous solvent or combination of solvents prior to use. To be suitable, the solvent must (1) be miscible with the storage stabilizing agent at the concentration of the latter, (2) have a sufficiently high vapor pressure to be readily removed by evaporation, (3) not appreciably affect the integrity of the polymeric article and (4) be capable, in combination with the storage stabilizing agent, of wetting the surface of the surgical article. Applying these criteria to a preferred storage stabilizing agent, glycerol and calcium lactate, lower alcohols such as methanol and ethanol are entirely suitable solvent carriers.

Preparing the storage stabilizing agent of the present invention is a relatively simple procedure. For example, in the case of glycerol and calcium lactate, the desired amount of glycerol is first introduced to a container, followed by the addition thereto of the desired amount of calcium lactate. If no solvent is to be used, the mixture is then thoroughly mixed. In the event a solvent is desired, the solvent such as methanol is added to the mixture of glycerol and calcium lactate and the solution is then thoroughly mixed to dissolve the compounds.

Generally, the stabilizing agent of the present invention is comprised of a mixture of a compound within formula (I) hereinabove, such as calcium lactate, and a water soluble hydroscopic polyhydroxy compound, such as glycerol, in a weight ratio of between about 1:1 to about 1:10, most preferably 1:7, respectively. When a solvent, such as methanol, is utilized in the preparation of the stabilizing agent, the solvent is employed in amounts to provide a solution concentration of from about 20% to about 50%, preferably about 30% to about 45%, based on the total weight of the solution.

Application of the storage stabilizing agent to the polymeric article can be carried out in any number of ways. Thus, for example, the article can be submerged in the storage stabilizing agent or solution thereof until at least a storage stabilizing amount of the stabilizing agent is acquired or otherwise retained by the article, even after the optional removal of any excess agent and/or accompanying solvent (if present) such as by drainage, wiping, evaporation, etc. In many cases, contact times on the order of from just a few seconds, e.g., about 10 seconds or so, to several hours, e.g., about 2 hours and even longer, are sufficient to impart a substantial improvement in the storage stability of the treated article compared to the same type of article which has not been treated with a storage stabilizing agent. In the case of a braided synthetic absorbable suture, it has been found that calendering the suture prior to filling, such as by passing the suture through at least two pairs of transversely mounted calender rolls, improves receptivity of the suture to filling and improves the suppleness of the resulting filled suture. It is believed that calendering the suture separates the individual suture filaments to open up spaces therebetween which are conductive to ensuring that the filling composition penetrates within and fills the interstices of the braided suture.

The foregoing submersion method of contacting the polymeric article with storage stabilizing agent can be conducted continuously or in batch. Thus, in the case of an absorbable suture, a running length of the suture can be continuously passed through a quantity of the stabilizing agent at a velocity which has been previously determined to provide the necessary degree of exposure, or contact time, of the suture with the storage stabilizing agent. As the suture emerges from the storage stabilizing agent, it can be passed through a wiper or similar device to remove excess agent prior to the packaging operation. Preferably, the suture is passed through a coating head supplied by a metering pump with a constant supply of filling solution, with the suture emerging from the coating head and passing through an evaporation oven to remove the filling solution solvent prior to any further surface contact, i.e. with rollers, etc. In a batch operation, a quantity of suture is merely submerged within the storage stabilizing agent for the requisite period of time with any excess agent being removed from the suture is desired.

Alternatively, the storage stabilizing agent and solutions thereof can be applied by spraying, brushing, wiping, etc., on the surfaces of the polymeric articles such that the latter receive and retain at least a storage stabilizing amount of the agent. Yet another procedure which can be used to apply the storage stabilizing agent involves inserting the polymeric article in a package containing an effective amount of the agent such that intimate contact between the polymeric article and the agent will be achieved.

Whatever the contacting procedure employed, it is necessary that the article being treated acquire a storage stabilizing amount of the storage stabilizing agent. In general, amounts of from about 2 to about 25, and preferable from about 5 to about 15 weight percent, of storage stabilizing agent (exclusive of any solvent) by weight of the polymeric article contacted therewith is sufficient to provide significantly improved storage stability compared to that of the untreated article.

As previously pointed out, braided, filled sutures in accordance with the invention need not be packaged and maintained under the very dry conditions required for prior synthetic absorbable sutures. Instead, it is preferred that the filled sutures be equilibrated so that the level of moisture or other stabilizing agent solvent is sufficient to result in an appropriate viscosity level for the stabilizing agent and thickener in order to keep the stabilizing agent on the suture. In the preferred embodiment of a braided suture filled with a mixture of glycerol and calcium lactate, the moisture level may be equilibrated to as low as about 0.2% by weight of the suture, and is preferably above 0.3% or, even more preferably, above 0.5% by weight of the suture.

Indeed, it has been found that the preferred sutures filled with glycerol calcium lactate undergo undesirable changes if exposed to a very dry environment. More particularly, if the sutures are exposed to a very dry environment, the surface of the suture accumulates a flaked or powdered substance on the surface thereof. It is believed such accumulation could interfere with removal of the suture or, at the very least, increase the force required to withdraw the suture from the retainer. Equilibrating the suture, such as in a dew point controlled environment, so that the suture contains a relatively high moisture level in excess of 0.2%, and preferably in excess of 0.5% by weight of the surgical suture, prevents the undesirable effects which would otherwise result if the sutures were to be exposed to an extremely dry environment. Conversely, the presence of too much moisture can also have deleterious effects, such as causing the glycerol filling to run. Therefore, it is preferable to control the moisture level within a range, such as 0.5 to 0.7% by weight of the suture.

In order to ensure consistent force to remove the suture from the retainer and prevent undesirable changes in the surgical article due to moisture level variations, it is desired to maintain the moisture of the suture within a close range of the original packaged value, and to prevent any significant variation of the moisture level, up or down, during storage after the package has been sealed. Notwithstanding the foil laminate construction of the preferred peelable pouch, moisture may permeate the peelable adhesive line of the peelable pouch to enter or leave the pouch after it has been sealed. For example, it is contemplated that sutures shipped to a desert environment might undesirably lose moisture through the seal line and, conversely, moisture may enter the pouch in a very humid environment. In either case, undesirable variation of the moisture level in the pouch and force to remove the suture may result.

Figure 13:
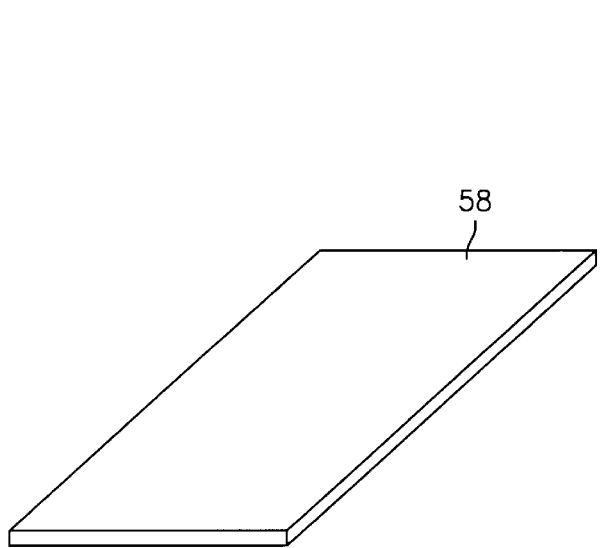
FIG. 13 is a perspective view of the preferred package stabilizing element.

To prevent such variations, a package stabilizing element is packaged in the pouch with the surgical article, i.e. the suture in the retainer. The package stabilizing element 58 is illustrated in FIG. 13, and may constitute a pad impregnated with the same stabilizing agent composition used to fill the suture. The package stabilizing element preferably is inserted into the peelable pouch prior to sterilization, and is sterilized, aerated and equilibrated with the filled suture and sealed within the pouch.

Figure 14:
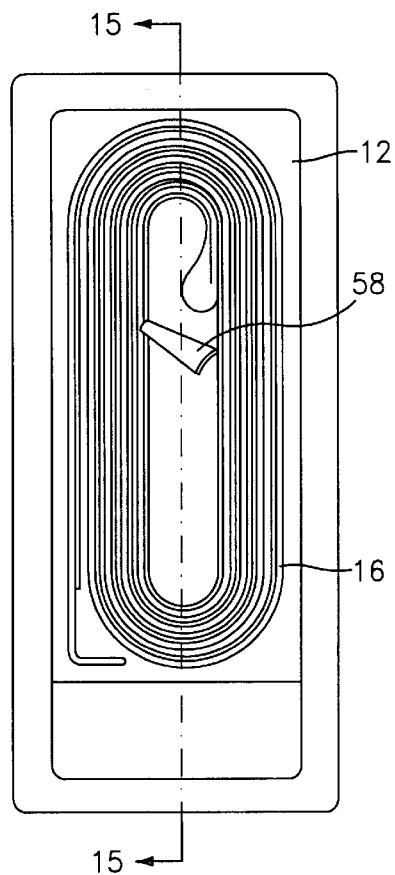
FIG. 14 is a plan view of a retainer and package stabilizing element.
Figure 15:
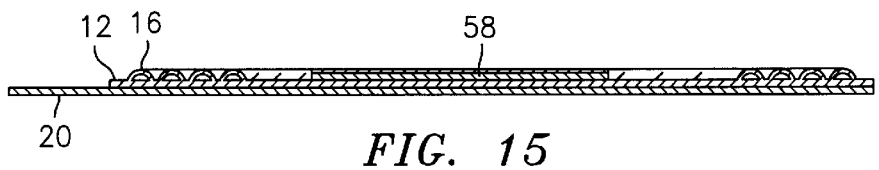
FIG. 15 is a cross-section view of the retainer of FIG. 14 taken along lines 15—15 of FIG. 14.
Figure 16:
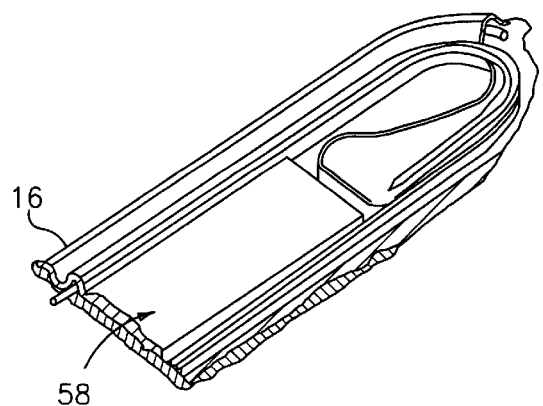
FIG. 16 is a partial perspective section view of the retainer and package stabilizing element of FIG. 14.

Referring now to FIGS. 14–16, package stabilizing element 58 preferably is centrally located on the suture retainer surrounded by spiral passageway 16, although any location within the envelope or peelable pouch is acceptable. Package stabilizing element 58 may comprise a sheet of medical grade cardboard, paper or other celulosic material filled with stabilizing agent. As in the case of the stabilizing agent for filling sutures, the stabilizing agent used to fill the pad preferably is a mixture of glycerol and calcium lactate, such as in a ratio of between about 1:1 to about 10:1, most preferably 7:1, respectively. The stabilizing agent may be applied to the pad in any acceptable manner, such as by spraying, soaking, dipping, etc. By way of example only, for suture packaging the package stabilizing element may be a sheet of medical grade cardboard measuring about 0.4 inches by 1.5 inches containing about 70 milligrams of stabilizing agent, such as 60 milligrams glycerol and 8.6 milligrams calcium lactate distributed so as to provide about 107 milligrams per square inch glycerol and 15 milligrams per square inch calcium lactate. For non-suture polymeric articles of greater mass a larger package stabilizing element containing a larger amount of stabilizing agent may be required.

It also can be advantageous to apply one or more coating compositions to the storage stabilized article of this invention to improve functional properties such as surface lubricity and knot tie-down behavior. A variety of suture coating compositions proposed for either or both purposes are known in the art, e.g. those disclosed in U.S. Pat. Nos. 3,867,190; 3,942,532; 4,047,533; 4,452,973; 4,624,256; 4,649,920; 4,716,203; and 4,826,945. It is contemplated that the coating could be applied to the suture either before or after filling. Suitable results have been obtained by coating the suture prior to filling, and thereafter calendering the suture to ensure optimum filling of the coated suture.

It is also within the scope of this invention to impregnate the braided suture with, or otherwise apply thereto, one or more medico-surgically useful substances, e.g., those which accelerate or beneficially modify the healing process when the suture is applied to a wound or surgical site. So, for example, the suture herein can be provided with a therapeutic agent which will be deposited at the sutured site. The therapeutic agent can be chosen for its antimicrobial properties, capability for promoting wound repair and/or tissue growth or for specific indications such as thrombosis. Antimicrobial agents such as broad spectrum antibiotics (gentamicin sulphate, erythromycin or derivatized glycopeptides) which are slowly released into the tissue can be applied in this manner to aid in combating clinical and sub-clinical infections in a surgical or trauma wound site.

To promote wound repair and/or tissue growth, one or more biologically active materials known to achieve either or both of these objectives can be applied to the suture. Such materials include any of several Human Growth Factors (HGFs), magainin, tissue or kidney plasminogen activator to cause thrombosis, superoxide dismutase to scavange tissue damaging free radicals, tumor necrosis factor for cancer therapy, colony stimulating factor, interferon, interleukin-2 or other lymphokine to enhance the immune system, and so forth.

The term "Human Growth Factor" or "HGF" embraces those materials, known in the literature, which are referred to as such and includes their biologically active closely related derivatives. The HGFs can be derived from naturally occurring sources including human and non-human sources, e.g., bovine sources, and are preferably produced by recombinant DNA techniques. Specifically, any of the HGFs which are mitogenically active and as such are effective in stimulating, accelerating, potentiating or otherwise enhancing the wound healing process can be usefully applied to the suture herein, e.g., hEGF (urogastrone), TGF-beta, IGF, PDGD, FGF, etc. These and other useful HGFs and closely related HGF derivatives, methods by which they can be obtained and methods and compositions featuring the use of HGFs to enhance wound healing are variously disclosed, inter alia, in U.S. Pat. Nos. 3,883,497; 3,917,824; 3,948,875; 4,338,397; 4,418,691; 4,528,186; 4,621,052; 4,743,679; 4,717,717; 4,961,757 and 4,874,746 European Patent Applications 0 046 039, 0 128 733, 0 131 868, 0 136 490, 0 147 178, 0 150 572, 0 177 915 and 0 267 015, PCT International Applications WO 83/04030, WO 85/003698, WO 85/01284 and WO 86/02271 and UK Patent Applications GB 2 092 155 A, 2 162 851 A and GB 2 172 890 A, and "Growth Factors in Wound Healing", Lynch, et. al. J. Clin. Invest. Vol. 84, pages 640–646 (August 1989), all of which are incorporated by reference herein. Of the known HGFs, hEGF, TGF-beta, IGF, PDGF and FGF are preferred, either singly or in combination.

In accordance with the disclosure of commonly assigned, copending Hermes et al. U.S. patent application Ser. No. 397,476, filed Aug. 18, 1989, the entire contents of which are hereby incorporated by reference, a filling composition comprising a surgical wound healing enhancing amount of at least one HGF and as carrier therefor at least one water soluble, liquid polyhydroxy compound and/or ester thereof such as any of those previously mentioned is applied to the suture. The carrier protects the HGF component of the filling composition from excessive degradation or loss of biopotency during storage and, when the suture is fabricated from an absorbable resin which is susceptible to hydrolysis, the carrier also constitutes the stabilizing agent for improving the storage stability of the suture. In addition to carrier, the HGF can contain a thickener such as any of those previously mentioned in order to reduce or limit the tendency of carrier run-off.

The filling composition can contain one or more additional components which promote or enhance the wound healing effectiveness of the HGF component. Thus, e.g., site-specific hybrid proteins can be incorporated in the filling composition to maximize the availability of the HGF at the wound site and/or to potentiate wound healing. See, e.g., Tomlinson (Ciba-Geigy Pharmaceuticals, West Sussex, U.K.), "Selective Delivery and Targeting of Therapeutic Proteins", a paper presented at a symposium held Jun. 12–14, 1989 in Boston, Mass., the contents of which are incorporated by reference herein. The HGFs can also be associated with carrier proteins (CPs), e.g., in the form of CP-bound HGF(s), to further enhance availability of the HGF(s) at a wound site as disclosed in "Carrier Protein-Based Delivery of Protein Pharmaceuticals", a paper of BioGrowth, Inc., Richmond, Calif. presented at the aforementioned symposium, the contents of said paper being incorporated by reference herein. The HGFs can also be incorporated in liposomes to provide for their release over an extended period. Lactate ion can be present to augment the wound healing activity of the HGF. Protectants for the HGF can also be utilized, e.g., polyethylene glycols, acetoxyphenoxy polyethoxy ethanols, polyoxyethylene sorbitans, dextrans, albumin, poly-D-alanyl peptides and N-(2-hydroxypropyl)-methacrylamide (HPMA).

The types and amounts of HGF, carrier and optional component(s) such as thickener, site-specific hybrid protein, carrier protein, etc., identified above can vary widely and in general will be at least that amount of a particular component which is required to perform its respective function in an effective way. Those skilled in the art employing known or conventional procedures can readily determine optimum amounts of each component for a particular filling composition and particular braided suture filled therewith.

In general, the HGF(s) can be present in the total composition at a level ranging from about 0.1 to about 25,000 micrograms per gram of such composition, preferably from about 0.5 to about 10000 micrograms per gram of composition and most preferably from about 1 to about 500 micrograms per gram of composition.

Application of the HGF-containing composition to the suture can be carried out by any suitable technique, e.g., by any of the procedures described above for applying a storage stabilizing agent to the suture.

The following examples are illustrative of the storage stabilizing method and storage stabilized polymeric article of this invention.

EXAMPLE 1

Glycerol filled and glycerol/calcium lactate filled braided sutures were centrifuged using a Clay Adams bench top lab centrifuge in order to compare retention as a percentage of baseline fill. Four samples were spun after collecting baseline data on the uncentrifuged sample. The centrifuge was run for 15 minutes at top speed, centrifugal force 3,000 Gs. The results are shown in Table I.

TABLE III

| | | Uncentrifuged | | Centrifuged | | % Retention | |
|---|---|---|---|---|---|---|---|
| Sample | | wt % G | wt % CaL | wt % G | wt % CaL | G | CaL |
| A: | Size 3/0 Synthetic Absorbable Suture | 21.7 | — | 10.5 ± 3 | — | 48 ± 14 | — |
| B: | Size 1/0 Synthetic Absorbable Suture | 3.4 | 2.7 | 3.3 | 2.8 | about 100 | about 100 |
| C: | Size 3/0 Synthetic Absorbable Suture | 14.9 | 2.2 | 12.9 | 1.7 | 87 | 78 |
| D: | Size 3/0 Synthetic Absorbable Suture | 15.4 | 3.8 | 9.9 | 2.7 | 64 | 71 |

G = glycerol
CaL = calcium lactate 5 $H_2O$
absorbable sutures = fibers from glycolide/lactide copolymers The foregoing data indicate that adding calcium lactate to glycerol gives an increase in glycerol retention.

EXAMPLE 2

Samples of calcium lactate/glycerol—filled braided sutures show equally improved stability to storage compared to glycerol filled braid without calcium lactate as shown in Table IV (Compare C and D to A and E). In both cases, the stability is excellent compared to braid without glycerol and equilibrated at about the same moisture level.

TABLE IV

| Sample | C | D | A | E | F |
|---|---|---|---|---|---|
| % Glycerin | 14.9 | 15.4 | 21.7 | 10 | -0- |
| % Ca lactate | 2.2 | 3.8 | -0- | -0- | -0- |
| % Water | 0.55 | 0.55 | 0.45 | 0.45 | 0.45 |

| Storage Time in weeks at 56° C. | % Strength Retained After 2 Weeks In Vitro at 37° C. After Accelerated Storage at 56° C. | | | | |
|---|---|---|---|---|---|
| 0 | 50 | 50 | 50 | 50 | 50 |
| 1 | 64 | 55 | 53 | 54 | 35 |
| 2 | 53 | 56 | 50 | 39 | 13 |
| 3 | 49 | 50 | 45 | 32 | 22 |
| 4 | 65 | 56 | 39 | 36 | 15 |
| 5 |  |  |  | 36 | 43 |
| 6 |  |  |  | 36 | 11 |

The following examples demonstrate the properties, characteristics and advantages of filled braided synthetic absorbable sutures packaged in accordance with the invention. All moisture analyses were performed on a Mitsubishi Moisture Meter Model CA-05 with a water vaporizer Model VA-05 attachment and a transfer time of no more than five seconds.

EXAMPLE 3

Braided Size 0 sutures composed of 90 percent mol weight glycolide and 10 percent mol weight lactide were prepared in thirty inch lengths and attached to needles by swaging. One set of sutures were filled with 10% glycerol and 1.2% calcium lactate by weight of the suture, and coated with the copolymerization product of polyalkylene glycol and a copolymer of 18% glycolide, 82% lactide. A second set of sutures were not filled or coated. All sutures were inserted by vacuum draw into the preferred molded retainers shown in FIGS. 1–3 constructed as described above of molded PETG with a TYVEK cover sheet adhered thereto with Oliver 18B hot melt adhesive. One half of each set of sutures was sterilized in an ethylene gas sterilization cycle and aerated to remove ethylene oxide residuals. The sterilized filled samples were equilibrated in an environment having a dew point of about −10° C. Each retainer was mounted in the vise of an Instron tester. Using a crosshead speed of 10 inches per minute and a full scale load of one pound, the maximum, peak load to withdraw both the sterilized and unsterilized sutures from the package was recorded. The results are set out in Table V.

TABLE V

| FORCE TO REMOVE SUTURE FROM MOLDED RETAINER (POUNDS) | | | |
|---|---|---|---|
| Unfilled Sutures | | Filled Sutures | |
| Pre-steril. | Post-steril. | Pre-steril. | Post-steril./equil. |
| 0.63 | * | 0.30 | 0.68 |
| 0.69 | * | 0.25 | 0.90 |
| 1.03 | * | 0.36 | 0.64 |
| 0.88 | * | 0.16 | 0.55 |
| 0.31 | * | 0.18 | 0.53 |
| 1.09 | * | 0.46 | 0.66 |
| 0.94 | * | 0.20 | 0.72 |
| 0.91 | * | 0.26 | 0.84 |
| 1.06 | * | 0.34 | 0.68 |

TABLE V-continued

| FORCE TO REMOVE SUTURE FROM MOLDED RETAINER (POUNDS) | | | |
|---|---|---|---|
| Unfilled Sutures | | Filled Sutures | |
| Pre-steril. | Post-steril. | Pre-steril. | Post-steril./equil. |
| 0.53 | * | 0.20 | 0.61 |
| 0.84 | * | 0.22 | 0.80 |
| 0.47 | 1.44 | 0.25 | 0.94 |
| Average 0.78 | — | 0.27 | 0.71 |

*Needle pulled off or suture broke.

The results shown in Table V show that unfilled uncoated braided size 0 sutures, packaged in the preferred retainer, could not be removed from the retainer after sterilization and equilibration. Thus, the presence of a filling composition, such as the preferred glycerol calcium lactate filling, appears to be necessary to obtain satisfactory withdrawal of the suture from the retainer.

EXAMPLE 4

Thirty inch lengths of size 3/0 braided sutures were prepared. One set of sutures was filled with 11.3% glycerol and coated with 2.9% of the coating described in Example 3, both by weight of the suture. A second set of sutures was filled with 1.9% calcium lactate and 11.2% glycerol and coated with 2.8% coating, all by weight of the suture. Equal numbers of samples were inserted into the retainers of Example 3 and equilibrated under different moisture conditions and sealed in foil laminate envelopes. The Group A samples were equilibrated to about 10° C. dew point. The Group B samples were equilibrated in the range of about −10° to −8° C. dew point, and the Group C samples were equilibrated to a range of about −14° to −12° C. dew point. The Group B samples filled with glycerol had a measured moisture content of about 0.58% by weight of the suture. The Group C samples filled with glycerol and calcium lactate had a moisture content of about 0.55%. The force in pounds to remove the equilibrated sutures from the package are set out in Table VI.

TABLE VI

| FORCE TO REMOVE SUTURE (POUNDS) | | | | | |
|---|---|---|---|---|---|
| G Filled | | | G-CaL Filled | | |
| A | B | C | A | B | C |
| 0.29 | 0.30 | 0.23 | 0.45 | 0.41 | 0.41 |
| 0.20 | 0.27 | 0.45 | 0.40 | 0.44 | 0.41 |
| 0.39 | 0.23 | 0.25 | 0.38 | 0.32 | 0.44 |
| 0.27 | 0.26 | 0.28 | 0.29 | 0.50 | 0.44 |
| 0.26 | 0.48 | 0.31 | 0.25 | 0.31 | 0.58 |
| 0.31 | 0.34 | 0.25 | 0.23 | 0.38 | 0.44 |
| 0.27 | 0.38 | 0.23 | 0.22 | 0.47 | 0.55 |
| 0.40 | 0.38 | 0.25 | 0.42 | 0.38 | 0.55 |
| 0.35 | 0.28 | 0.27 | 0.41 | 0.53 | 0.28 |
| 0.35 | 0.25 | 0.33 | 0.37 | 0.70 | 0.48 |
| Ave. 0.31 | 0.32 | 0.28 | 0.34 | 0.44 | 0.46 |

These results show that as the equilibration conditions become drier, the glycerol calcium lactate filled sutures become more difficult to remove from the molded retainer. While not intending to be bound by theory, it is believed that, as conditions become drier, calcium lactate accumulates in a powdery or flaked form at or near the surface of the suture, and inhibits removal of the suture from the retainer.

Thus, in addition to other factors, a balance must be struck between the amount of calcium lactate and moisture level.

EXAMPLE 5

Size 0 braided synthetic absorbable sutures of various lengths filled with 9.0% glycerol and 1.3% calcium lactate and coated with 2.8% of the preferred coating were inserted into the retainer illustrated in FIGS. 1–3 described above. The sutures were sterilized, aerated, equilibrated in an environment controlled at about −10° C. dew point until the sutures contained approximately 0.46% by weight moisture, and sealed in bulk in a foil laminate envelope container. The force to withdraw the various sutures lengths from the retainer was measured and is reported, in pounds, in Table VII.

TABLE VII

| Suture Removal Force (Pounds) vs. Length | | | | | |
|---|---|---|---|---|---|
| 15" | 18" | 21" | 24" | 27" | 30" |
| 0.04 | 0.04 | 0.10 | 0.33 | 0.30 | 0.54 |
| 0.02 | 0.03 | 0.07 | 0.24 | 0.27 | 0.68 |
| 0.02 | 0.03 | 0.09 | 0.22 | 0.20 | 0.64 |
| 0.02 | 0.08 | 0.06 | 0.20 | 0.28 | 0.56 |
| 0.01 | 0.04 | 0.16 | 0.23 | 0.35 | 0.37 |
| 0.01 | 0.03 | 0.06 | 0.22 | 0.27 | 0.58 |
| 0.01 | 0.04 | 0.06 | 0.10 | 0.30 | 0.54 |
| 0.01 | 0.03 | 0.10 | 0.15 | 0.23 | 0.64 |
| 0.02 | 0.03 | 0.06 | 0.19 | 0.30 | 0.50 |
| 0.02 | | 0.06 | 0.11 | 0.27 | 0.51 |
| | | | | 0.36 | |
| AVE. 0.02 | 0.04 | 0.08 | 0.20 | 0.29 | 0.56 |

Figure 17:
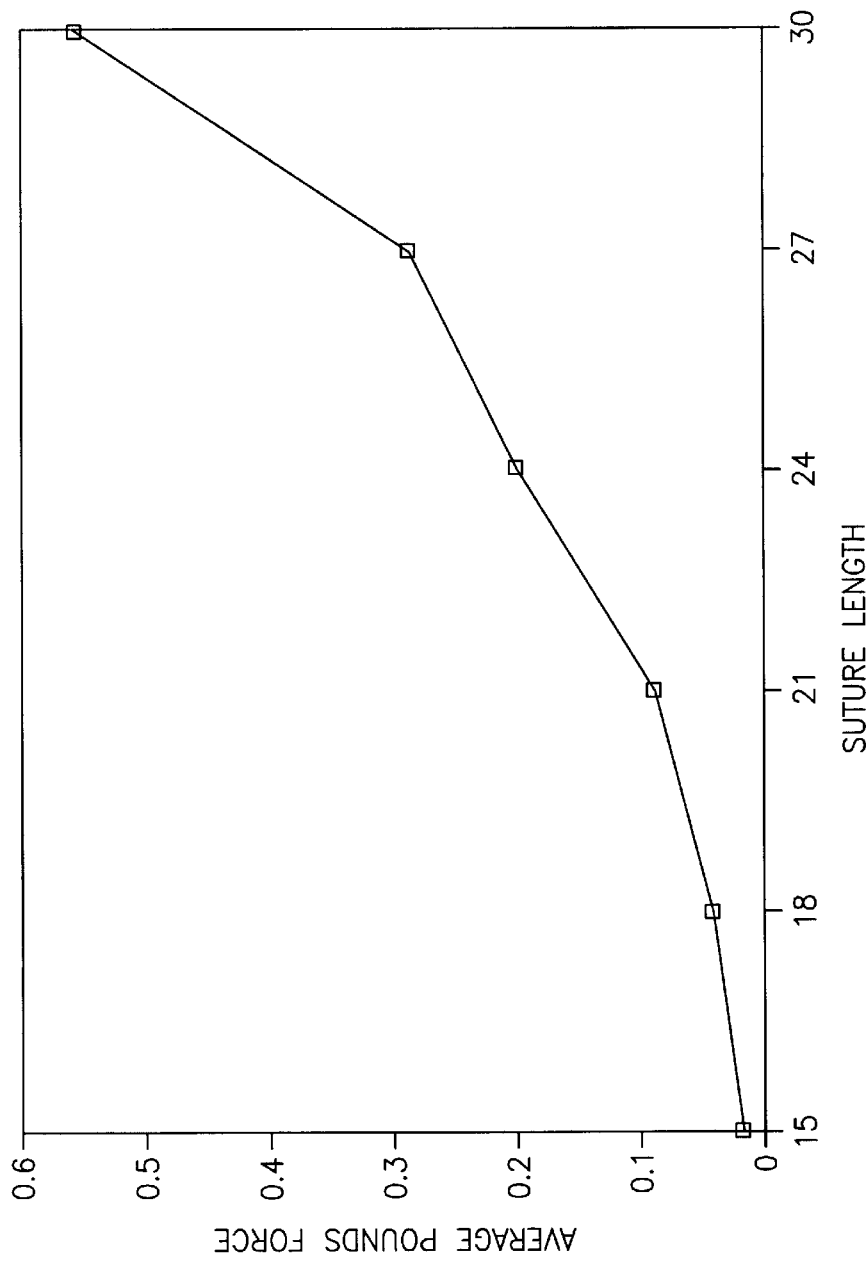
FIG. 17 is a graph illustrating force to remove sutures of various lengths from the preferred molded retainer.

The average force to remove each suture from the retainer is plotted in FIG. 17. From this data it may be concluded that relatively long lengths of suture may be packaged in the preferred retainer with acceptable suture withdrawal forces. For consistent, easy removal, it has been found the optimum force to remove the suture from the retainer should in all cases be below about 0.20 kilograms. In order to accommodate smaller size sutures, particularly those of the variety having releasable needles, it is favorable to further limit the suture withdrawal force. Thus, the optimum force to withdraw the suture should not exceed about 0.02 kilograms for a size 8/0 suture, 0.04 kilograms for a size 7/0 suture, 0.08 kilograms for a size 6/0 suture, and 0.12 kilograms for a size 5/0 suture.

EXAMPLE 6

Braided filled sutures were prepared in thirty inch lengths. Single sutures were loaded full length into the retainer of FIGS. 1–3, doubled and tripled over into the retainer of FIGS. 3 and 6–7. The sutures were sterilized aerated and equilibrated. All sutures were then sealed in foil pouches. The force to withdraw the sterile sutures from the retainers was measured and the results are reported in Table VIII.

TABLE VIII

| Force to Remove Coiled, Doubled-over and Tripled-over Sutures (Pounds) | | |
|---|---|---|
| Coiled | Tripled-over | Doubled-over |
| .96 | .08 | .46 |
| .88 | .11 | .61 |
| 1.21 | .18 | 1.28 |
| .88 | .08 | .54 |
| 1.03 | .11 | .41 |

TABLE VIII-continued

| Force to Remove Coiled, Doubled-over and Tripled-over Sutures (Pounds) | | |
|---|---|---|
| Coiled | Tripled-over | Doubled-over |
| .91 | .09 | .43 |
| .88 | .22 | .57 |
| 1.24 | .14 | .43 |
| .99 | .09 | .49 |
| 1.23 | | .38 |
| 1.18 | | .31 |
| .91 | | .34 |
| .76 | | .30 |
| .82 | | 1.02 |
| 1.56 | | .78 |
| 1.19 | | |
| .90 | | |
| 1.31 | | |
| Ave. 1.05 | .12 | .56 |

Thus, the average force to remove a doubled-over thirty inch suture is approximately one-half the force required to pull-out a full length coiled suture. The average force to remove the tripled-over suture was roughly one-tenth the force to remove the full-length suture.

EXAMPLE 7

Ten samples of size 3/0 sutures filled with a glycerol calcium lactate mixture were sterilized; aerated, equilibrated and sealed in peelable pouches with a package stabilizing element consisting of a paper sheet impregnated with approximately 60 milligrams of a glycerol/calcium lactate stabilizing agent having a weight ratio of 6.5:1 glycerin to calcium lactate. Ten samples of size 3/0 sutures packaged without the stabilizing element were selected for comparative testing. Absorbable sutures fabricated from a copolymer of glycolide and lactide were used. These sutures had an average weight of 0.06 g per suture. All samples were equilibrated at −10 to −8° C. dew point before sealing. Water was added to the packages of each group through a vent hole in the package using a microliter syringe and the vent hole immediately sealed. The samples were labeled with the amount of water added and allowed to stand for 72 hours to allow for equilibration in the packet. At thin time, the sutures and the stabilizing element were tested for moisture and compared to the control which was sealed without the addition of water. The data shown in Table IX illustrate the percent weight in moisture of the sutures packaged with the package stabilizing element as compared with sutures packaged without the stabilizing element when various increments of water were added.

TABLE IX

ADDED MOISTURE STUDY
Initial moisture content: suture with stabilizing element = .53%
stabilizing element = 1.62%
suture without stabilizing element = 0.59%

| | | Wt. % | |
|---|---|---|---|
| Water Added | No Stabilizing Element | Suture with Stabilizing Element | |
| (ug) | Suture | Suture | Stabilizing Element |
| 0 | 0.57 | 0.59 | 1.67 |
| 200 | 0.64 | 0.61 | 1.74 |
| 500 | 0.66 | 0.59 | 1.85 |
| 1000 | 0.78 | 0.64 | 1.90 |

TABLE IX-continued

ADDED MOISTURE STUDY
Initial moisture content: suture with stabilizing element = .53%
stabilizing element = 1.62%
suture without stabilizing element = 0.59%

| | Wt. % | | |
|---|---|---|---|
| Water Added | No Stabilizing Element | Suture with Stabilizing Element | |
| (ug) | Suture | Suture | Stabilizing Element |
| 2000 | 0.96 | 0.64 | 2.30 |
| 3000 | 0.97 | 0.74 | 2.59 |
| 4000 | 1.52 | 0.80 | 3.06 |
| 5000 | 1.87 | 1.12 | 3.80 |
| 7000 | 2.49 | 1.09 | 4.22 |
| Slope | $2.7 \times 10^{-4}$/ug | $8.1 \times 10^{-5}$%/ug | $3.8 \times 10^{-4}$%/ug |

The data show that, for a size 3/0 suture the moisture content will increase by 0.00027% for each microgram (ug) of water added while the same suture, when packaged with the package stabilizing element will increase by only 0.000081%. These numbers are for size 3/0 suture and will vary accordingly to the size of the suture.

EXAMPLE 8

The amount of water contained in the suture and the stabilizing agent was calculated from the data presented above in Example 7. Total moisture in the suture was directly read from the raw data, total moisture in the stabilizing agent was calculated based on an average dry weight of 0.167 g per stabilizing element. The added water content of each component at each increment was determined by subtracting the initial total water from the total water found after water addition. It was assumed that the packaging absorbed all water not found in the suture or the stabilizing element.

TABLE X

ADDED WATER DISTRIBUTION
Initial suture without stabilizing element - 352 ug $H_2O$
Initial suture with stabilizing element - 361 ug $H_2O$
Initial stabilizing element - 2790 ug $H_2O$

| | Suture w/Stabilizing Element | | | | | | | | |
|---|---|---|---|---|---|---|---|---|---|
| | Suture | | Stabilizing Element | | Package | | Suture | | Package |
| Water Added | ug Added | % | ug Added | % | ug Added | % | ug Added | % | ug Added | % |
| 200 ug | 28 | 14 | 116 | 58 | 56 | 28 | 52 | 26 | 148 | 74 |
| 500 ug | 4 | 1 | 300 | 60 | 196 | 39 | 66 | 13 | 434 | 87 |
| 1000 ug | 41 | 4 | 383 | 38 | 576 | 58 | 147 | 15 | 853 | 85 |
| 2000 ug | 49 | 2 | 1051 | 53 | 900 | 45 | 265 | 13 | 1735 | 87 |
| 3000 ug | 106 | 4 | 1535 | 51 | 1359 | 45 | 255 | 9 | 2745 | 91 |
| 4000 ug | 147 | 4 | 2320 | 58 | 1533 | 38 | 633 | 16 | 3367 | 84 |
| 5000 ug | 350 | 7 | 3564 | 71 | 1086 | 22 | 848 | 17 | 4152 | 83 |
| 7000 ug | 340 | 5 | 4257 | 61 | 2403 | 34 | 1236 | 18 | 5764 | 82 |

Examples 7 and 8 demonstrate that the package stabilizing element substantially reduces the range of variation in moisture content in the suture which might otherwise result due to moisture entering the pouch. Similar results are expected in relation to moisture leaving the foil pouch, but would be more difficult and time consuming to test. Thus, the moisture content of the suture is maintained very close to the relatively high level present at the time the pouch is sealed, and varies only very slightly as moisture enters or leaves the pouch. In the context of the preferred molded retainer having a convoluted passageway, the filled suture is protected against the effects of moisture entering or leaving the pouch, and the force to remove the suture from the retainer remains substantially constant. It in also contemplated that the package stabilizing element may have similar advantages in the packaging of other types of hydrolyzable surgical articles containing or associated with a stabilizing agent. Types of articles include vascular grafts, bone screws, staples, clips, splints, ligaments, drug delivery systems, etc.

The package stabilizing element also has other significant advantages. For example, a glycerol based stabilizing agent has a tendency to migrate and coat the entire surface of a closed container such as the peelable pouch. The presence of the package stabilizing element including a relatively large quantity of stabilizing agent provides an alternative source of glycerol for migration. It has been found that inclusion of the package stabilizing element in the closed package reduces lose due to migration of a glycerol based stabilizing agent material from the surgical article, i.e. the filled suture. This desirable result also contributes to the consistent force required to remove the suture from the package by ensuring a substantially constant amount of glycerol in the filled suture.

As stated, prior synthetic absorbable sutures packaged in the conventional "figure 8" configuration in a cardboard retainer under very dry conditions undesirably retain kinks and bends when removed from the retainer and do not exhibit good hand and feel characteristics which are so important to the end user. The preferred braided, filled synthetic absorbable sutures packaged in accordance with the invention synergistically provide a remarkably supple, flexible suture which is readily removed from the package and has desirable hand and feel as removed from the package. Advantageously, the convolutions of the preferred molded retainer also enhance the flexibility and suppleness of the sutures prepared in accordance with the invention by flexing the suture as it is withdrawn from the retainer. Although it is difficult to quantify the characteristics of good hand and feel, several tests have been developed in an attempt to do so.

In the first test, a vertical hanging test, the suture is removed from the package and simply allowed to hang under gravity. The hanging length of the suture is measured and compared to the full, straightened length of the suture. The result is expressed as percent of straightened length.

Figure 18:
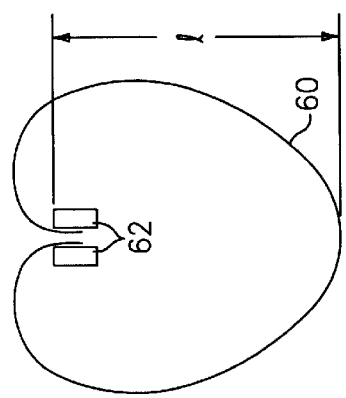
FIG. 18 is a diagram of a suture mounted for heart loop testing.

The second test is a hanging "heart loop" test based on ASTM D 1388. In this test, the suture is removed from the package and one and of the suture is taped to a bar. Holding the suture taut, the other end of the suture is taped to a second bar. The bars are mounted in a test fixture in the configuration shown in FIG. 18 so that the suture 60 assumes the heart shaped loop configuration supported by the bars 62. The suture is allowed to hang vertically for one minute, and the distance "l" from the top of the mounting bars to the bottom of the suture loop is recorded. The bending length of the suture is calculated, consistent with ASTM D 2388, according to the following formula:

$$C = l_o F(O)$$

where:

l=loop length in centimeters $l_0 = 0.1337$ L

L=suture strip length, i.e. the distance between the bars when the suture is mounted, in centimeters.

$f(O) = (\cos O / \tan O)^{1/3}$ $O = 32.85 \, d/l_o$, in degrees, and $d = l - l_O$ The third test uses a Gurley Stiffness Tester Model 4171, in a test method similar to that described in U.S. Pat. No. 3,630,205. Multiple two inch suture segments are prepared with minimal handling and are inserted into a holding fixture and clamped so that one and one-half inches of each strand protrudes from the bottom of the fixture. The fixture is mounted in the Gurley instrument so that the bottom of the gage lies one-half inch above the edge of the swinging pendulum. The apparatus in operated through one or two cycles (a left owing plus a right swing) to adjust the weight distance so that the average Gurley unit is between 2.0 and 7.0. The apparatus is then operated for 5 cycles without recording results. The readings of cycles 6 through 10 are recorded and averaged. The stiffness of the suture is calculated as follows:

$$\text{Stiffness, grams} = \text{weight used} \times \frac{\text{scale reading}}{10} \times \text{arm distance}$$

The preferred number of strands and test weight and distance are set out for each suture size in Table XI.

TABLE XI

Gurley Test Parameters

| Suture Size | Number of Strands | Weight (grams) | Weight Distance (Inches) |
|---|---|---|---|
| 2 | 8 | 5 | 1 |
| 1 | 8 | 5 | 1 |
| 0 | 8 | 5 | 1 |
| 1/0 | 8 | 5 | 1 |
| 2/0 | 8 | 5 | 1 |
| 3/0 | 8 | 5 | 1 |
| 4/0 | 8 | .5 | 2 |
| 5/0 | 15 | .5 | 2 |
| 6/0 | 24 | .5 | 2 |
| 7/0 | 45 | .5 | 2 |

EXAMPLE 9

Various sizes of braided filled sutures were made, packaged in the retainer of FIGS. 1–3 and the preferred mid-peel pouch, equilibrated and sealed in accordance with the invention. Upon removal from the package the sutures were tested using the vertical hanging test, the heart loop test and Gurley stiffness test. The results are set out in Tables XII through XIV.

TABLE XII

Braided Filled Sutures
Vertical Hanging Test

| Size | Sample | Length as is (cm) | Length Straightened (cm) | % Straight Length |
|---|---|---|---|---|
| 2 | 1 | 62.8 | 68.4 | 92.0 |
|   | 2 | 68.5 | 73.9 | 93.0 |
|   | 3 | 61.7 | 68.5 | 90.0 |
|   | 4 | 62.6 | 68.1 | 92.0 |
|   | 5 | 62.3 | 68.3 | 91.0 |
|   | 6 | 62.1 | 68.1 | 91.0 |
|   | 7 | 61.3 | 68.7 | 89.0 |
|   | 8 | 62.5 | 68.0 | 92.0 |
|   | 9 | 61.5 | 68.5 | 90.0 |
|   | 10 | 61.5 | 68.4 | 90.0 |
|   |   |   | Ave.: | 91.0 |
| 1 | 1 | 63.4 | 68.4 | 92.7 |
|   | 2 | 64.2 | 68.5 | 93.7 |
|   | 3 | 62.3 | 68.3 | 91.2 |
|   | 4 | 62.2 | 68.5 | 90.8 |
|   | 5 | 62.0 | 68.5 | 90.5 |
|   | 6 | 66.2 | 70.7 | 93.6 |
|   | 7 | 67.4 | 71.2 | 94.7 |
|   | 8 | 67.5 | 71.1 | 94.9 |
|   | 9 | 69.0 | 74.1 | 93.1 |
|   | 10 | 68.8 | 72.0 | 95.6 |
|   |   |   | Ave.: | 93.1 |
| 1 | 1 | 63.0 | 69.0 | 91 |
|   | 2 | 66.5 | 68.9 | 97 |
|   | 3 | 65.0 | 68.6 | 95 |
|   | 4 | 63.0 | 68.5 | 92 |
|   | 5 | 64.0 | 69.0 | 93 |
|   |   |   | Ave.: | 94 |
| 0 | 1 | 66.8 | 72.4 | 92.3 |
|   | 2 | 67.0 | 72.5 | 92.4 |
|   | 3 | 67.5 | 72.9 | 92.6 |
|   | 4 | 65.6 | 71.8 | 91.4 |
|   | 5 | 66.9 | 72.1 | 92.8 |
|   | 6 | 65.5 | 71.2 | 92.0 |
|   | 7 | 66.9 | 72.4 | 92.4 |
|   | 8 | 67.3 | 72.6 | 92.7 |
|   | 9 | 66.8 | 72.6 | 92.0 |
|   | 10 | 62.7 | 67.1 | 93.4 |
|   |   |   | Ave.: | 92.4 |
| 0 | 1 | 65.7 | 75.8 | 87 |
|   | 2 | 63.3 | 76.2 | 83 |
|   | 3 | 61.5 | 76.2 | 81 |
|   | 4 | 59.5 | 76.1 | 78 |
|   | 5 | 57.0 | 76.0 | 75 |
|   | 6 | 59.9 | 76.6 | 78 |
|   |   |   | Ave.: | 80 |
| 2/0 (No Stabilizing element in pckg.) | 1 | 75.5 | 76 | 99 |
|   | 2 | 68.5 | 75.5 | 91 |
|   | 3 | 71.2 | 76.5 | 93 |
|   | 4 | 70.0 | 74.5 | 94 |
|   | 5 | 68.5 | 75.5 | 91 |
|   |   |   | Ave.: | 94 |
| 3/0 | 1 | 73.0 | 75.9 | 96.2 |
|   | 2 | 70.8 | 74.5 | 95.0 |
|   | 3 | 73.1 | 76.6 | 95.4 |
|   |   |   | Ave.: | 95.5 |
| 5/0 | 1 | 62.1 | 68.9 | 90.1 |
|   | 2 | 61.2 | 69.3 | 88.3 |
|   | 3 | 61.5 | 68.6 | 90.0 |
|   | 4 | 59.1 | 68.8 | 86.0 |
|   | 5 | 59.0 | 68.9 | 85.6 |
|   | 6 | 61.0 | 68.6 | 89.0 |
|   | 7 | 61.5 | 68.6 | 89.6 |
|   | 8 | 61.4 | 68.7 | 89.3 |

TABLE XII-continued

Braided Filled Sutures
Vertical Hanging Test

| Size | Sample | Length as is (cm) | Length Straightened (cm) | % Straight Length |
|---|---|---|---|---|
| | 9 | 61.0 | 68.5 | 89.0 |
| | 10 | 58.5 | 68.3 | 85.6 |
| | | | Ave.: | 88.3 |
| 5/0 | 1 | 67.0 | 75.0 | 89 |
| | 2 | 68.0 | 75.0 | 90 |
| | 3 | 67.5 | 74.5 | 91 |
| | 4 | 67.5 | 75.2 | 90 |
| | 5 | 68.2 | 75.9 | 90 |
| | | | Ave.: | 90 |

TABLE XIII

Braided Filled Sutures
Heart Loop Test

| Size | Sample | Loop length | Bending length |
|---|---|---|---|
| 2 | 1 | 8.80 | 2.54 |
| | 2 | 8.40 | 2.74 |
| | 3 | 6.20 | 3.95 |
| | 4 | 8.40 | 2.74 |
| | 5 | 7.20 | 3.36 |
| | 6 | 6.20 | 3.95 |
| | 7 | 6.40 | 3.82 |
| | 8 | 7.20 | 3.36 |
| | 9 | 6.60 | 3.70 |
| | 10 | 9.00 | 2.44 |
| | | Ave.: | 3.26 |
| 1 | 1 | 6.4 | 3.82 |
| | 2 | 7.4 | 3.25 |
| | 3 | 6.4 | 3.82 |
| | 4 | 6.6 | 3.70 |
| | 5 | 6.0 | 4.09 |
| | 6 | 6.2 | 3.95 |
| | 7 | 8.2 | 2.84 |
| | 8 | 6.4 | 3.82 |
| | 9 | 8.2 | 2.84 |
| | 10 | 7.0 | 3.47 |
| | | Ave.: | 3.56 |
| 1 | 1 | 4.6 | 5.50 |
| | 2 | 8.4 | 2.74 |
| | 3 | 6.6 | 3.70 |
| | 4 | 7.2 | 3.36 |
| | 5 | 7.4 | 3.25 |
| | 6 | 7.6 | 3.14 |
| | 7 | 6.6 | 3.70 |
| | 8 | 7.0 | 3.47 |
| | 9 | 7.4 | 3.25 |
| | 10 | 8.8 | 3.54 |
| | | Ave.: | 3.47 |
| 0 | 1 | 6.2 | 3.95 |
| | 2 | 8.6 | 2.64 |
| | 3 | 7.2 | 3.36 |
| | 4 | 8.0 | 2.94 |
| | 5 | 7.0 | 3.47 |
| | 6 | 7.8 | 3.04 |
| | 7 | 7.6 | 3.14 |
| | 8 | 5.2 | 4.76 |
| | 9 | 7.0 | 3.47 |
| | 10 | 7.2 | 3.36 |
| | | Ave.: | 3.41 |
| 0 | 1 | 9.2 | 2.33 |
| | 2 | 9.2 | 2.33 |
| | 3 | 9.8 | 2.03 |
| | 4 | 9.6 | 2.13 |
| | 5 | 9.2 | 2.33 |
| | 6 | 10.0 | 1.92 |
| | | Ave.: | 2.17 |

TABLE XIII-continued

Braided Filled Sutures
Heart Loop Test

| Size | Sample | Loop length | Bending length |
|---|---|---|---|
| 2/0 (No stabilizing element in package) | 1 | 8.40 | 2.74 |
| | 2 | 9.20 | 2.33 |
| | 3 | 8.40 | 2.74 |
| | 4 | 8.80 | 2.54 |
| | 5 | 9.20 | 2.33 |
| | | Ave.: | 2.54 |
| 3/0 | 1 | 9.00 | 2.44 |
| | 2 | 9.40 | 2.23 |
| | 3 | 8.80 | 2.54 |
| | | Ave.: | 2.40 |
| 5/0 | 1 | 6.60 | 3.70 |
| | 2 | 7.40 | 3.25 |
| | 3 | 7.60 | 3.14 |
| | 4 | 6.40 | 3.82 |
| | 5 | 7.00 | 3.47 |
| | 6 | 7.00 | 3.47 |
| | 7 | 7.40 | 3.25 |
| | 8 | 7.60 | 3.14 |
| | 9 | 7.60 | 3.14 |
| | 10 | 7.80 | 3.04 |
| | | Ave.: | 3.34 |
| 5/0 | 1 | 6.2 | 3.95 |
| | 2 | 7.2 | 3.36 |
| | 3 | 7.2 | 3.36 |
| | 4 | 7.4 | 3.25 |
| | 5 | 8.0 | 2.94 |
| | | Ave.: | 3.37 |

TABLE XIV

Braided Filled Sutures
Gurley Stiffness

| Size (weight, grams) (distance, inches) | Sample | Scale reading (Ave. of 5 measurements) |
|---|---|---|
| 2 (5) (2) | 1 | 4.58 |
| | 2 | 4.86 |
| | 3 | 3.94 |
| | 4 | 4.4 |
| | 5 | 4.46 |
| | Ave.: | 4.45 |
| | Stiffness: | 4.45 |
| 1 (5) (1) | 1 | 3.9 |
| | 2 | 4.58 |
| | 3 | 4.48 |
| | 4 | 4.46 |
| | 5 | 4.28 |
| | Ave.: | 4.34 |
| | Stiffness: | 2.17 |
| 1 (5) (1) | 1 | 4.1 |
| | 2 | 4.5 |
| | Ave.: | 4.3 |
| | Stiffness: | 2.15 |
| 0 (5) (1) | 1 | 3.38 |
| | 2 | 3.16 |
| | Ave.: | 3.27 |
| | Stiffness: | 1.64 |
| 0 (5) (1) | 1 | 5.3 |
| | 2 | 5.3 |
| | 3 | 5.6 |
| | 4 | 5.0 |
| | 5 | 5.0 |
| | 6 | 5.2 |
| | Ave.: | 5.23 |
| | Stiffness: | 2.62 |
| 2/0 (5) (1) | 1 | 3.72 |
| | 2 | 3.88 |
| | 3 | 3.78 |

TABLE XIV-continued

Braided Filled Sutures
Gurley Stiffness

| Size<br>(weight, grams)<br>(distance, inches) | Sample | Scale reading<br>(Ave. of 5 measurements) |
|---|---|---|
| (No stabiliz- | 4 | 3.70 |
| ing element | 5 | 3.70 |
| in package) | Ave.: | 3.76 |
|  | Stiffness: | 1.88 |
| 3/0 | 1 | 3.6 |
| (.45) | 2 | 3.3 |
| (2) | 3 | 2.58 |
|  | Ave.: | 3.16 |
|  | Stiffness: | .28 |
| 5/0 | 1 | 3.9 |
| (1.50) | 2 | 4.7 |
| (1) | 3 | 4.9 |
|  | 4 | 4.7 |
|  | 5 | 4.3 |
|  | Ave.: | 4.5 |
|  | Stiffness: | .68 |
| 5/0 | 1 | 4.54 |
| (1.5) | 2 | 2.56 |
| (1) | 3 | 4.3 |
|  | 4 | 5.28 |
|  | 5 | 4.74 |
|  | Ave.: | 4.28 |
|  | Stiffness: | .64 |

EXAMPLE 10

For purposes of comparison, Ethicon Vicryl site 0 braided absorbable sutures were tested for out of package vertical hang and Gurley stiffness,. Because the Vicryl sutures exhibited too many kinks or "sets" they could not be tested using the heart loop test.

TABLE XV

Vicryl Size 0
Vertical Hanging Test

| Sample No. | Length as is | Length<br>Straightened | % Straight<br>Length |
|---|---|---|---|
| 1 | 39.7 | 70.1 | 57 |
| 2 | 37.5 | 70.2 | 53 |
| 3 | 37.4 | 69.9 | 54 |
| 4 | 42.2 | 69.7 | 61 |
| 5 | 46.5 | 70.1 | 66 |
|  |  | Ave.: | 58% |

TABLE XVI

Vicryl Size 0
Gurley Stiffness
(5 gram weight - 2 inch distance)

| Test | Scale reading<br>(Average 5 measurements) |
|---|---|
| 1 | 4.52 |
| 2 | 5.38 |
| 3 | 5.10 |
| 4 | 5.48 |
| 5 | 6.26 |
| Ave.: | 5.35 |
| Stiffness: | 5.35 |

EXAMPLE 11

Vicryl Size 3-0 braided absorbable sutures were tested. The sutures had 63% vertical hang. Gurley stiffness is set out in Table XVII.

TABLE XVII

Vicryl Size 3-0
Gurley Stiffness
(1.5 gram weight - 1 inch distance)

| Test | Scale Reading<br>(Ave. of 5 measurements) |
|---|---|
| 1 | 5.6 |
| 2 | 4.7 |
| Ave.: | 5.15 |
| Stiffness: | 5.15 |

EXAMPLE 12

The braided filled sutures in accordance with the invention display remarkable suppleness and flexibility comparable to the feel and hand of braided silk sutures. For comparison, commercially available braided silk sutures from Davis & Geck, American Cyanamid Co. were tested for Gurley stiffness. The results set out in Table XVIII, as compared to Table XIV, show that the synthetic absorbable sutures in accordance with the invention display flexibility and suppleness comparable to silk sutures.

TABLE XVIII

BRAIDED SILK
GURLEY STIFFNESS

| Suture Size | Gurley Stiffness (Ave.) |
|---|---|
| 2 | 3.4 |
| 1 | 2.5 |
| 0 | 3.13 |
| 2-0 | 2.5 |
| 3-0 | 1.09 |
| 4-0 | 0.30 |
| 5-0 | .44 |
| 6-0 | .18 |
| 7-0 | .07 |

In summary braided filled synthetic absorbable sutures packaged in accordance with the invention display an out of package hanging length greater than about 80% of actual length, a bending length of about 3.00, and Gurley stiffness lose than 5.00. Indeed, sutures of the invention have a Gurley stiffness comparable to braided silk sutures.

EXAMPLE 13

Figure 19:
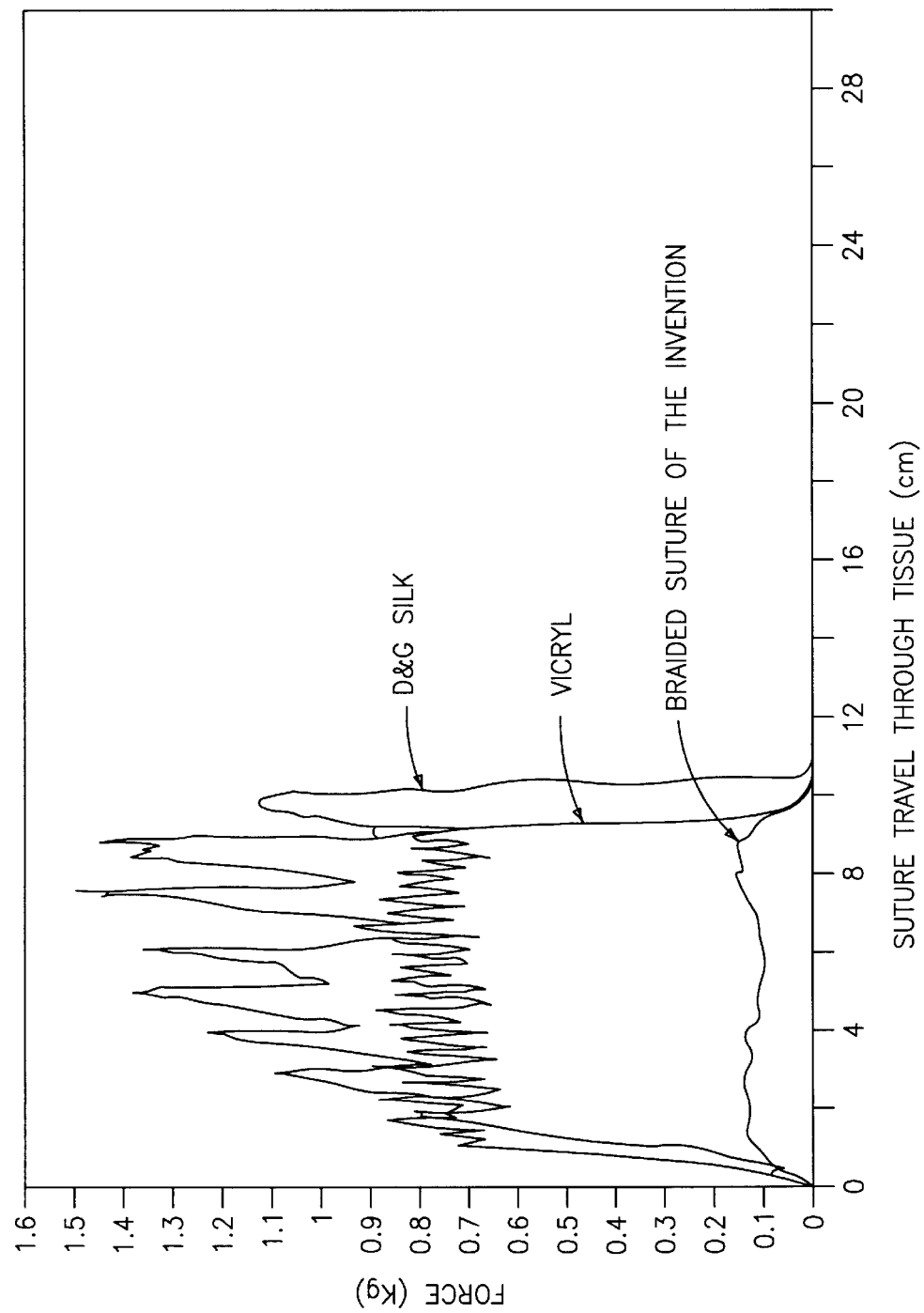
FIG. 19 is a graphical representation of the out of package tissue drag performance of a braided filled suture packaged in accordance with the invention compared with that of two known types of braided sutures of equivalent size.

A size 2/0 braided suture possessing structural characteristics as described in Tables I and II coated with the preferred coating described in Example 3 was filled with a mixture of glycerin calcium lactate and packaged in a retainer substantially as shown in FIGS. 1–3 within the peelable pouch of FIGS. 11–12. The suture was sterilized, moisture equilibrated and sealed. Post-sterility testing showed that the suture contained 10.1% glycerin, 1.7% calcium lactate and 3.4% coating. The suture was removed from the package and was compared with & size 2/0 braided silk suture of Davis A Cock, Inc. ("D & G Silk") and a Vicryl size 2/0 braided absorbable suture for tissue drag. The tissue drag profiles of the three sutures appear in FIG. 19 as the plot of force (kg) required to pull each suture through abdominal animal fascia tissue through a distance of somewhat greater than 10 cm. As the graphically represented data show, the braided filled suture constructed in accordance with the principles of this invention exhibited a dramatically reduced level of tissue drag compared to either of the other two standard sutures.

The foregoing examples demonstrate the superiority of the braided, filled sutures packaged in accordance with the invention in comparison to commercially available packaged synthetic absorbable sutures, and that the packaged sutures in accordance with the present invention display superior handling and tissue drag characteristics.

To the extent not already indicated, it also will be understood by those of ordinary skill in the art that any one of the various specific embodiments heroin described and illustrated may be further modified to incorporate features shown in other of the specific embodiments.

The invention in its broader aspects therefore is not limited to the specific embodiments herein shown and described but departures may be made therefrom within the scope of the accompanying claims without departing from the principles of the invention and without sacrificing its chief advantages.

What is claimed is:

1. The combination of
   a) a peelable substantially moisture-impervious pouch made of a metal foil laminate defining an enclosure which constitutes a sealed pocket and which is accessible by peeling;
   b) a suture retainer disposed within said sealed pocket and sealed therewithin; and
   c) a synthetic absorbable suture situated within said retainer.

2. The combination of claim 1 wherein said suture is composed of a majority of glycolide.

3. The combination of claim 2 wherein said suture (c) comprises a glycolide content of at least approximately 90% mole weight.

4. The combination of claim 1 wherein said suture retainer member is manufactured from hard plastic material.

5. The combination of claim 1 wherein said suture retainer member comprises a flat panel having a first surface and a second surface, with a suture-retaining labyrinth mounted upon said second surface.

6. The combination of claim 1 wherein said retainer member comprises a multiple panel retainer in folded condition and enclosing said synthetic absorbable surgical suture.

7. The combination of claim 1 being structured and arranged such that said suture enclosed in said pouch remains stable for a plurality of weeks and until said flap is peeled open.

8. The combination of
   a) a peelable substantially moisture-impervious pouch made of a metal foil laminate defining an enclosure accessible by peeling;
   b) a molded plastic suture retainer having a curved passageway and disposed and sealed within said sealed pocket of said peelable pouch; and
   c) a sterile synthetic absorbable suture susceptible to hydrolysis disposed within said retainer passageway.

9. The combination of claim 8 being structured and arranged such that said suture remains stable for a plurality of weeks and until said flap is peeled open.

10. The combination of claim 8 wherein said suture (c) is composed of a major amount of glycolide.

11. The combination of claim 8 wherein said suture (c) comprises a glycolide content of at least approximately 90% mole weight.

12. The combination of claim 1, herein said pouch and retainer are formed and positioned with respect to one another, such that when said pouch is peeled open, said pouch and retainer are not torn open.

13. The combination of claim 8, wherein said pouch and retainer are formed and positioned with respect to one another, such that when said pouch is peeled open, said pouch and retainer are not torn open.

14. The combination of claim 1, additionally comprising a needle coupled to said suture, and said combination components a), b) and c) being structured and arranged such that immediately upon peeling said pouch, said needle is revealed and accessible in a single step without tearing the retainer.

15. The combination of claim 8, additionally comprising a needle coupled to said suture, and said combination components a), b) and c) being structured and arranged such that immediately upon peeling said pouch, said needle is revealed and accessible in a single step without tearing the retainer.

16. The combination of claim 1, wherein said suture retainer b) is disposed immediately within said sealed pocket a).

17. The combination of claim 8, wherein said suture retainer b) is disposed immediately within said sealed pocket a).

18. The combination of
   a) a peelable substantially moisture-impervious pouch made of a metal foil laminate defining an enclosure which constitutes a sealed pocket and which is accessible by peeling;
   b) a suture retainer disposed within said sealed pocket and sealed therewithin;
   c) a synthetic absorbable suture situated within said retainer; and
   d) an outer breather pouch in which said moisture-impervious pouch a) is disposed and sealed.

19. The combination of claim 18, wherein said outer breather pouch d) is peelable.

20. The combination of claim 18, wherein said suture retainer b) is disposed immediately within said sealed pocket a).

* * * * *